(12) United States Patent
Hirsch-Weil et al.

(10) Patent No.: US 9,908,862 B2
(45) Date of Patent: Mar. 6, 2018

(54) METHODS OF PRODUCING ALKYLFURANS

(71) Applicant: MICROMIDAS, INC., West Sacramento, CA (US)

(72) Inventors: Dimitri A. Hirsch-Weil, Sacramento, CA (US); Makoto N. Masuno, Elk Grove, CA (US); John Bissell, Sacramento, CA (US); Dennis A. Hucul, Midland, MI (US); Alex B. Wood, Sacramento, CA (US); Robert Joseph Araiza, Sacramento, CA (US); Daniel R. Henton, Midland, MI (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 14/912,052

(22) PCT Filed: Aug. 15, 2014

(86) PCT No.: PCT/US2014/051209
§ 371 (c)(1),
(2) Date: Feb. 12, 2016

(87) PCT Pub. No.: WO2015/023918
PCT Pub. Date: Feb. 19, 2015

(65) Prior Publication Data
US 2016/0200700 A1 Jul. 14, 2016

Related U.S. Application Data

(60) Provisional application No. 61/866,491, filed on Aug. 15, 2013.

(51) Int. Cl.
*C07D 307/36* (2006.01)
*C07D 307/34* (2006.01)

(52) U.S. Cl.
CPC ........ *C07D 307/36* (2013.01); *C07D 307/34* (2013.01)

(58) Field of Classification Search
None
See application file for complete search history.

(56) References Cited

U.S. PATENT DOCUMENTS

| 4,335,049 | A | 6/1982 | Hamada et al. |
| 2011/0263880 | A1* | 10/2011 | Rauchfuss ........... C07D 307/36 549/506 |
| 2014/0171699 | A1 | 6/2014 | Wang et al. |

FOREIGN PATENT DOCUMENTS

| CN | 101434588 B | 8/2011 |
| EP | 2666540 A1 | 11/2013 |
| JP | 61-59633 B2 | 12/1986 |
| WO | 2015/023918 A2 | 2/2015 |
| WO | 2015/031753 A1 | 3/2015 |
| WO | 2016/025865 A1 | 2/2016 |

OTHER PUBLICATIONS

Yinghuai, Z. et al article in Applications of Ionic Liquids in Science and Technology, 2011, Handy, S. ed., pp. 3-27.*
Albers et al., "Poisoning and Deactivation of Palladium Catalysts", Journal of Molecular Catalysis A: Chemical, vol. 173, 2001, pp. 275-286.
Binder et al., "Simple Chemical Transformation of Lignocellulosic Biomass into Furans for Fuels and Chemicals", Journal American Chemical Society, vol. 131, No. 5, 2009, pp. 1979-1985.
Boudart, M., "Turnover Rates in Heterogeneous Catalysis", Chemical Reviews, vol. 95, No. 3, 1995, pp. 661-666.
Boyer et al., "Mild Hydrogen-Transfer Reductions Using Sodium Hypophosphite", J. Org. Chem., vol. 50, No. 18, 1985, pp. 3408-3411.
Brunner, Erwin, "Solubility of Hydrogen in 10 Organic Solvents at 298.15, 323.15, and 373.15 K", Journal of Chemical and Engineering Data, vol. 30, No. 3, 1985, pp. 269-273.
Chatterjee et al., "Hydrogenation of 5-Hydroxymethylfurfural in Supercritical Carbon Dioxide—Water: a Tunable Approach to Dimethylfuran Selectivity", Green Chemistry, vol. 16, 2014, pp. 1543-1551.
Chidambaram et al., "A Two-Step Approach for the Catalytic Conversion of Glucose to 2,5-Dimethylfuran in Ionic Liquids", Green Chemistry, vol. 12, 2010, pp. 1253-1262.
Delidovich et al., "Alternative Monomers Based on Lignocellulose and Their Use for Polymer Production", Chemical Reviews, vol. 116, 2016, pp. 1540-1599.
Deutsch et al., "Active Species of Copper Chromite Catalyst in C—O Hydrogenolysis of 5-Methylfurfuryl Alcohol", Journal of Catalysis, vol. 285, 2012, pp. 235-241.
Dutta et al., "Novel Pathways to 2,5-Dimethylfuran via Biomass-Derived 5-(Chloromethyl) Furfural", Chemsuschem, vol. 7, 2014, pp. 3028-3030.
Hamada et al., "Novel Synthetic Route to 2,5-Disubstituted Furan Derivatives through Surface Active Agent-Catalyzed Dehydration of D-(-)-Fructose", J. Oleo Sci., vol. 50, No. 6, 2001, pp. 533-536. (English Abstract Submitted).
Harmon et al., "Hydrogenation of Organic Compounds Using Homogeneous Catalysts", Chemical Reviews, vol. 73, No. 1, 1973, pp. 21-52.
Iqbal et al., "Conversion of Furfuryl Alcohol into 2-Methylfuran at Room Temperature using Pd/Ti02 Catalyst", Catalysis Science & Technology, vol. 4, 2014, pp. 2280-2286.

(Continued)

*Primary Examiner* — Heidi Reese
(74) *Attorney, Agent, or Firm* — Morrison & Foerster LLP

(57) ABSTRACT

Provided herein are methods of producing dialkylfurans, such as 2,5-dimethylfuran, and other alkyl furans, such as 2-methylfuran. For example, 2,5-dimethylfuran may be produced by reducing (5-methylfuran-2-yl)methanol or 2-(chloromethyl)-5-methylfuran.

29 Claims, 4 Drawing Sheets

(56) References Cited

OTHER PUBLICATIONS

Klusoň et al., "Ru-Sn CATALYST—A New Promising System for Selective Hydrogenation of a Carbonyl Group", Chem. Listy, vol. 91, 1997, pp. 100-104.
Kwon et al., "Electrocatalytic Hydrogenation of 5-Hydroxymethylfurfural in the Absence and Presence of Glucose", ChemSusChem, vol. 6, 2013, pp. 1659-1667.
Lange et al., "Furfural—A Promising Platform for Lignocellulosic Biofuels", ChemSusChem, vol. 5, 2012, pp. 150-166.
Lessard et al., "High Yield Conversion of Residual Pentoses into Furfural via Zeolite Catalysis and Catalytic Hydrogenation of Furfural to 2-Methylfuran", Topics in Catalysis, vol. 53, Sep. 2010, pp. 1231-1234.
Liu et al., "One-Pot Conversion of Carbohydrates into Furan Derivatives via Furfural and 5-Hydroxylmethylfurfural as Intermediates", ChemSusChem, vol. 9, 2016, pp. 2015-2036.
Luijkx et al., "Ether Formation in the Hydrogenolysis of Hydroxymethylfurfural over Palladium Catalysts in Alcoholic Solution", Heterocycles, vol. 77, No. 2, 2009, pp. 1037-1044.
Lund et al., "Electrochemical Reduction of Foran Derivatives Derived from Biomass", Acta Chemica Scandinavica, vol. 39 B, No. 6, 1985, pp. 429-435.
Luo et al., "Mechanisms for High Selectivity in the Hydrodeoxygenation of 5-Hydroxymethylfurfural over PtCo Nanocrystals", ACS Catalysis, vol. 6, 2016, pp. 4095-4104.
Luttringhaus et al., "Tetramethylurea as a Solvent and Reagent", Angew. Chem. International Edition, vol. 3, No. 4, 1964, pp. 260-269.
Marques et al., "Facile Hydrodehalogenation with H2 and Pd/C Catalyst under Multiphase Conditions. 3. Selective Removal of Halogen from Functionalized Aryl Ketones. 4. Aryl Halide-Promoted Reduction of Benzyl Alcohols to Alkanes", J. Org. Chem. vol. 60, No. 8, 1995, pp. 2430-2435.
Mascal et al., "Direct, High-Yield Conversion of Cellulose into Biofuel", Angewandte Chemie International Edition, vol. 47, 2008, pp. 7924-7926.
Mitra et al., "Pd/C-Catalyzed Reactions of HMF: Decarbonylation, Hydrogenation, and Hydrogenolysis", Green Chemistry, 2014, 7 pages.
Nakagawa et al., "Catalytic Reduction of Biomass-Derived Furanic Compounds with Hydrogen", ACS Catalysis, vol. 3, 2013, pp. 2655-2668.
Nishimura et al., "Selective Hydrogenation of Biomass-Derived 5-Hydroxymethylfurfural (HMF) to 2,5-Dimethylfuran (DMF) under Atmospheric Hydrogen pressure over Carbon Supported PdAu Bimetallic Catalyst", Catalysis Today, 2013, pp. 1-10.
International Preliminary Report on Patentability received for PCT Patent Application No. PCT/US2014/051209, dated Feb. 25, 2016, 7 pages.
International Search Report & Written Opinion received for PCT Patent Application No. PCT/US2014/051209, dated Nov. 13, 2014, 9 pages.
International Preliminary Report on Patentability received for PCT Patent Application No. PCT/US2015/045330, dated Mar. 2, 2017, 8 pages.
International Search Report and Written Opinion received for PCT Application No. PCT/US2015/045330, dated Nov. 20, 2015, 11 pages.
Pittman et al., "Sequential Catalytic Condensation-Hydrogenation of Ketones", J. Org. Chem. vol. 45, No. 25, 1980, pp. 5048-5052.
Román-Leshkov et al., "Production of Dimethylfuran for Liquid Fuels from Biomass-Derived Carbohydrates", Nature, vol. 447, Jun. 21, 2007, pp. 982-985.
Rosatella et al., "5-Hydroxymethylfurfural (HMF) as a Building Block Platform: Biological Properties, Synthesis and Synthetic Applications", Green Chemistry, vol. 13, 2011, pp. 754-793.
Schniepp et al., "The Preparation of Acetopropyl Alcohol and 1,4-Pentanediol from Methylfuran", J. Am. Chem. Soc., vol. 69, Mar. 1947, pp. 672-674.
Smith, Patrick B., "Bio-Based Sources for Terephthalic Acid", Green Polymer Chemistry: Biobased Materials and Biocatalysis, Chapter 27, 2015, pp. 453-469.
Stakheev et al., "Specific Features of the Catalytic Behavior of Supported Palladium Nanoparticles in Heterogeneous Catalytic Reactions", Russian Journal of General Chemistry, vol. 80, No. 3, 2010, pp. 618-629.
Thananatthanachon et al., "Efficient Production of the Liquid Fuel 2,5-Dimethylfuran from Fructose using Formic Acid as a Reagent", Angewandte Chemie International Edition, vol. 49, 2010, pp. 6616-6618.
Wei et al., "One-Pot Production of 2,5-Dimethylfuran from Fructose over Ru/C and a Lewis—Brønsted Acid Mixture in N,N-Dimethylformamide", Catalysis Science & Technology, vol. 6, 2016, pp. 6217-6225.
Yinghuai et al., "Ionic Liquids in Catalytic Biomass Transformation", Applications of Ionic Liquids in Science and Technology, 2011, pp. 3-27.
Zhang et al., "Highly Active Polymer Anchored Palladium Catalyst for the Hydrodehalogenation of Organic Halides under Mild Conditions", Tetrahedron Letters, vol. 35. No. 26, 1994, pp. 4599-4602.
Notice of Allowance received for U.S. Appl. No. 15/503,681, dated Aug. 1, 2017, 7 pages.
Chen et al., "Immobilized Ru Clusters in Nanosized Mesoporous Zirconium Silica for the Aqueous Hydrogenation of Furan Derivatives at Room Temperature", ChemCatChem, vol. 5, 2013, pp. 2822-2826.
Extended European Search Report (includes Supplementary European Search Report and Search Opinion) received for European Patent Application No. 15832265.1, dated Jan. 2, 2018, 10 pages.
Kumalaputri et al., "Tunable and Selective Conversion of 5-HMF to 2,5-Furandimethanol and 2,5-Dimethylfuran over Copper-Doped-Porous Metal Oxides", ChemSusChem, vol. 7, 2014, pp. 2266-2275.

* cited by examiner

METHODS OF PRODUCING ALKYLFURANS

CROSS REFERENCE TO RELATED APPLICATIONS

This application is a U.S. national stage of PCT/US2014/051209, filed Aug. 15, 2014, which claims the benefit of U.S. Provisional Patent Application Ser. No. 61/866,491, filed Aug. 15, 2013, the disclosure of which are hereby incorporated herein by reference in their entireties.

FIELD

The present disclosure relates generally to methods of producing dialkylfurans and other alkylfurans, and more specifically to methods of producing 2,5-dimethylfuran and 2-methylfuran.

BACKGROUND

Dialkylfurans, such as 2,5-dimethylfuran (DMF), and other alkylfurans have potential applications for use as biofuels. Several methods are known in the art to produce DMF. Current methods known in the art to produce DMF from other furan compounds have been challenging with respect to minimizing the furan ring reduction. Thus, what is needed in the art are methods of selectively reducing furan compounds to produce DMF.

BRIEF SUMMARY

Provided herein are methods to reduce furan compounds to produce alkylfurans. In some aspects, provided is a method of producing a compound of formula (I'):

(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
by reducing a compound of formula (A) to produce the compound of formula (I'), wherein the compound of formula (A) is:

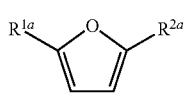
(A)

wherein:
R$^{1a}$ is C$_m$ alkyl, or —(CH$_2$)$_m$Y, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo.

In some embodiments, the compound of formula (A) is reduced to produce the compound of formula (I') in the presence of:
hydrogen,
a catalyst, and
a reagent of formula (i), (ii) or (iii), or any combinations thereof,
wherein:
the reagent of formula (i) is:

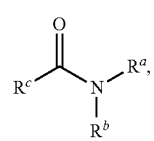
(i)

wherein:
each R$^a$, R$^b$ and R$^c$ is independently H, aliphatic, aryl, or heteroaryl; or
R$^a$ and R$^b$ are taken together with the nitrogen atoms to which they are connected to form a cyclic moiety having at least 3 ring atoms; and
the reagent of formula (ii) is:

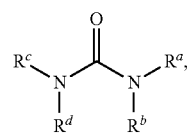
(ii)

wherein:
(A) each R$^a$, R$^b$, R$^c$ and R$^d$ is independently H, aliphatic, aryl or heteroaryl; or
(B) R$^a$ and R$^b$ are taken together with the nitrogen atoms to which they are connected to form a cyclic moiety having at least 3 ring atoms; and each R$^c$ and R$^d$ is independently H, aliphatic, aryl or heteroaryl; or
(C) each R$^a$ and R$^b$ is independently H, aliphatic, aryl or heteroaryl; and R$^c$ and R$^d$ are taken together with the nitrogen atoms to which they are connected to form a cyclic moiety having at least 3 ring atoms; or
(D) R$^a$ and R$^b$ are taken together with the nitrogen atoms to which they are connected to form a cyclic moiety having at least 3 ring atoms; and R$^c$ and R$^d$ are taken together with the nitrogen atoms to which they are connected to form a cyclic moiety having at least 3 ring atoms; or
(E) each R$^a$ and R$^c$ is independently H, aliphatic, aryl or heteroaryl; and R$^b$ and R$^d$ are taken together with the nitrogen atoms to which they are connected to form a cyclic moiety having at least 5 ring atoms; or
(F) each R$^b$ and R$^d$ is independently H, aliphatic, aryl or heteroaryl; and R$^a$ and R$^c$ are taken together with the nitrogen atoms to which they are connected to form a cyclic moiety having at least 5 ring atoms; and the reagent formula (iii) is:

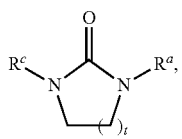

wherein:
  each $R^a$ and $R^c$ is independently H, aliphatic, aryl or heteroaryl; and
  t is an integer greater than or equal to 0.

In yet other aspects, provided is a method of producing a compound of formula (I'):

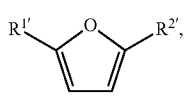

wherein:
  $R^{1'}$ is $C_m$ alkyl, wherein m is an integer greater than or equal to 0, provided that when m is 0, $R^{1'}$ is H; and
  $R^{2'}$ is $C_n$ alkyl, wherein n is an integer greater than or equal to 1, by:
  a) converting a compound of formula (B) to a compound of formula (C), wherein:
    the compound of formula (B) is:

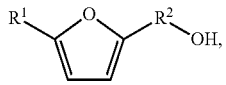

wherein:
  $R^1$ is $C_m$ alkyl, wherein m is as defined for formula (I'); and
  $R^2$ is —$(CH_2)_n$—, wherein n is as defined for formula (I'),
the compound of formula (C) is:

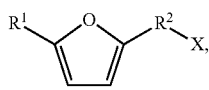

wherein:
  $R^1$ and $R^2$ are as defined for formula (B); and
  X is halo; and
  b) reducing the compound of formula (C) to produce the compound of formula (I').

In some variations, the compound of formula (C) is reduced to produce the compound of formula (I') in the presence of:
  hydrogen,
  a catalyst, and
  any one of reagents of formula (i), (ii) and (iii) described herein, or any combinations thereof.

In one aspect, provided is a method of producing 2,5-dimethylfuran, by:

a) providing (5-methylfuran-2-yl)methanol; and
b) selectively reducing the (5-methylfuran-2-yl)methanol to produce 2,5-dimethylfuran.

In some embodiments, the (5-methylfuran-2-yl)methanol is selectively reduced in the presence of hydrogen and a catalyst.

In another aspect, provided is a method of producing 2,5-dimethylfuran, by:
  a) providing (5-methylfuran-2-yl)methanol;
  b) converting the (5-methylfuran-2-yl)methanol to 2-(chloromethyl)-5-methylfuran in the presence of an acid; and
  c) selectively reducing the 2-(chloromethyl)-5-methylfuran to produce 2,5-dimethylfuran.

In some embodiments, the 2-(chloromethyl)-5-methylfuran is selectively reduced in the presence of hydrogen and a catalyst.

In other embodiments, the (5-methylfuran-2-yl)methanol is provided by:
  i) providing 5-methylfuran-2-carbaldehyde; and
  ii) converting the 5-methylfuran-2-carbaldehyde to (5-methylfuran-2-yl)methanol in the presence of acid, hydrogen and a catalyst.

In yet other embodiments, the (5-methylfuran-2-yl)methanol is provided by:
  i) providing 5-(chloromethyl)furfural;
  ii) converting the 5-(chloromethyl)furfural to 5-methylfuran-2-carbaldehyde in the presence of hydrogen and a catalyst; and
  iii) converting the 5-methylfuran-2-carbaldehyde in the presence of acid, hydrogen and a catalyst.

In one embodiment that may be combined with any of the preceding embodiments, the catalyst is a palladium catalyst.

In other aspects, provided herein are also compositions that include any of the compounds of formula (A), catalysts, hydrogen, and amine or urea reagents described herein. In some embodiments, the compositions may also include any of the acids and/or solvents described herein.

DESCRIPTION OF THE FIGURES

The present application can be best understood by reference to the following description taken in conjunction with the accompanying figures, in which like parts may be referred to by like numerals.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods of producing dialkylfurans, such as 2,5-dialkylfurans, and other alkylfurans, such as 2-alkylfurans.

Figure 1:
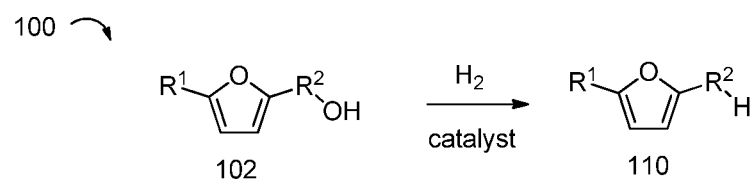
FIGS. 1 and 2 depict exemplary reaction schemes to produce a dialkylfuran.

For example, in one aspect, provided is a method of producing 2,5-dimethylfuran from (5-methylfuran-2-yl) methanol. With reference to FIG. 1, process 100 is an exemplary reaction scheme for producing dialkylfurans 110. In some embodiments, $R^1$ is alkyl, and $R^2$ is —$(CH_2)_n$—, where n is an integer and at least 1. In one embodiment, $R^1$ is methyl and $R^2$ is —$(CH_2)_n$—, such that compound 102 is (5-methylfuran-2-yl)methanol and compound 110 is 2,5-dimethylfuran. Compound 102 may be selectively reduced in the presence of hydrogen and a catalyst, such as palladium (Pd) catalyst. (5-Methylfuran-2-yl)methanol may be converted into 2,5-dimethylfuran by selectively reducing the alcohol functional group of (5-methylfuran-2-yl)methanol without reducing, or by minimizing the reduction of, the furan ring.

Figure 2:
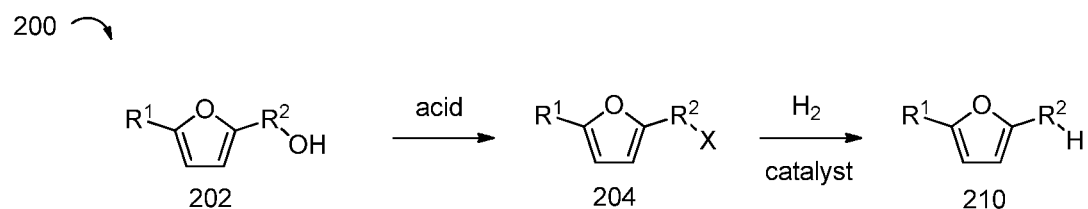

In another aspect, with reference to FIG. 2, process 200 is another exemplary reaction scheme for producing dialkylfurans 210. In some embodiments, $R^1$ is alkyl, and $R^2$ is —$(CH_2)_n$—, where n is an integer and at least 1. In one embodiment, $R^1$ is methyl and $R^2$ is —$(CH_2)_n$—, such that compound 202 is (5-methylfuran-2-yl)methanol, compound 204 is 2-(halomethyl)-5-methylfuran (wherein X is halo), and compound 210 is 2,5-dimethylfuran. (5-Methylfuran-2-yl)methanol may be converted under acidic conditions into 2-(halomethyl)-5-methylfuran, such as 2-(chloromethyl)-5-methylfuran. In one example, (5-methylfuran-2-yl)methanol may be reacted with hydrochloric acid and a salt (e.g., lithium chloride salt) to produce 2-(chloromethyl)-5-methylfuran. With reference again to FIG. 2, 2-(halomethyl)-5-methylfuran, such as 2-(chloromethyl)-5-methylfuran, may subsequently be converted into 2,5-dimethylfuran by selectively reducing the halide functional group of 2-(halomethyl)-5-methylfuran without reducing, or by minimizing the reduction of, the furan ring.

In some embodiments, compounds 102 (FIG. 1) and 202 (FIG. 2) may be obtained from any commercially available sources or produced according to any suitable methods known in the art.

Figure 3:
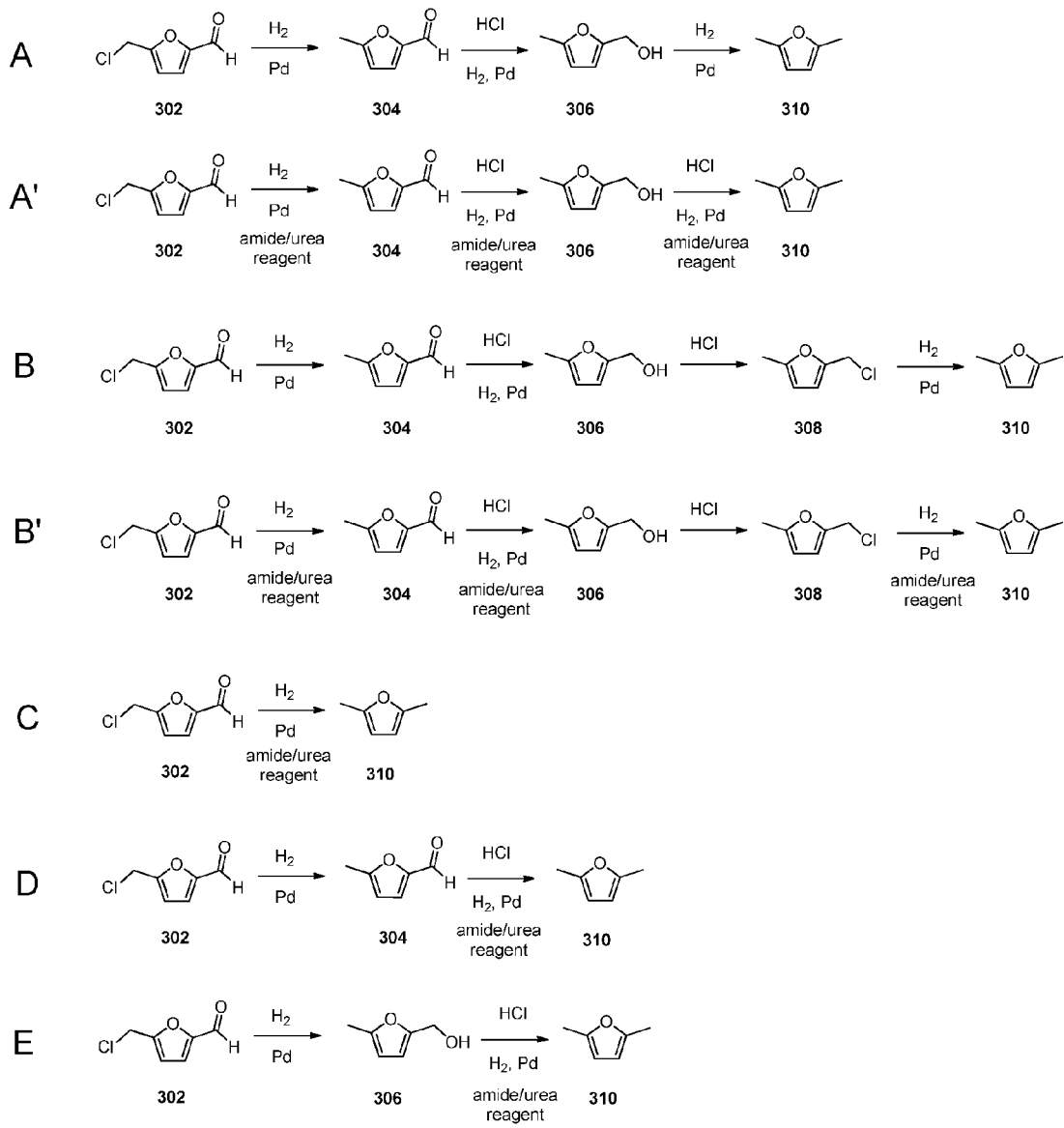
FIGS. 3A-3E depict exemplary reaction schemes to convert 2-(chloromethyl)furfural to 2,5-dimethylfuran.
Figure 5:
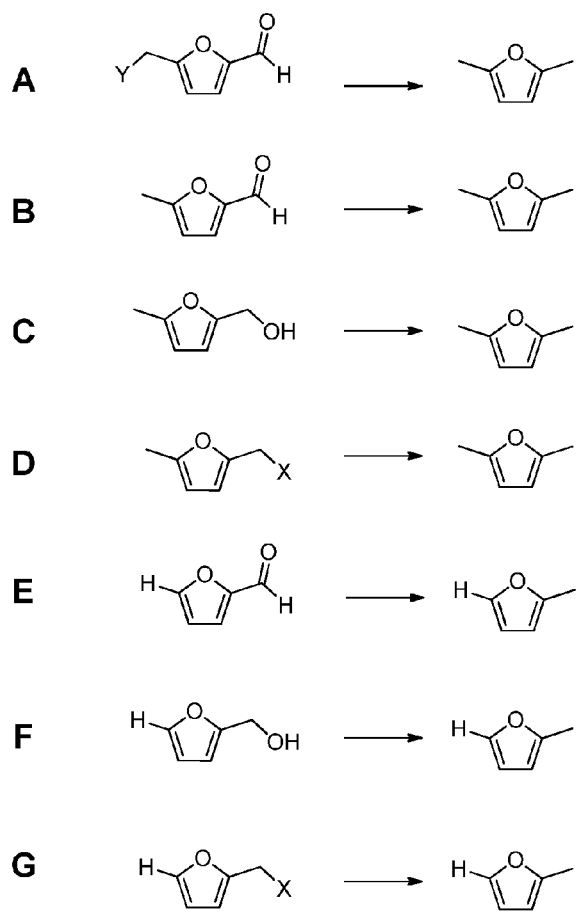
FIGS. 5A-5D depict exemplary reaction schemes to produce 2,5-dimethylfuran.
FIGS. 5E-5G depict exemplary reaction schemes to produce 2-methylfuran.

In other embodiments, for example, with reference to FIG. 3A, 5-(chloromethyl)furfural 302 may be converted to 5-methylfuran-2-carbaldehyde 304 in the presence of hydrogen and a catalyst, such as a palladium (Pd) catalyst. In one variation, with reference again to FIG. 3A, 5-methylfuran-2-carbaldehyde 304 may then be reacted with an acid, such as hydrochloric acid, in the presence of hydrogen and a metal catalyst, such as a palladium (Pd) catalyst, to produce (5-methylfuran-2-yl)methanol 306, which may then be reduced to form 2,5-dimethylfuran 310.

In another variation, with reference to FIG. 3A', 5-(chloromethyl)furfural 302 may be converted to 5-methylfuran-2-carbaldehyde 304 in the presence of hydrogen, a catalyst, such as a palladium (Pd) catalyst, and an amide or urea reagent as described herein. In one variation, with reference again to FIG. 3A', 5-methylfuran-2-carbaldehyde 304 may then be reacted with an acid, such as hydrochloric acid, in the presence of hydrogen, a metal catalyst, such as a palladium (Pd) catalyst, and an amide or urea reagent as described herein, to produce (5-methylfuran-2-yl)methanol 306, which may then be reduced to form 2,5-dimethylfuran 310. In certain variations, the catalyst used in FIGS. 3A and 3A' may be the same or different. In certain variations, the amide or urea reagent used in FIG. 3A' may be the same or different.

In yet other embodiments, with reference to FIG. 3B, 5-(chloromethyl)furfural 302 may be converted to 5-methylfuran-2-carbaldehyde 304 in the presence of hydrogen and a catalyst, such as a palladium (Pd) catalyst. 5-Methylfuran-2-carbaldehyde 304 may then be reacted with an acid, such as hydrochloric acid, in the presence of hydrogen and a metal catalyst, such as a palladium (Pd) catalyst, to produce (5-methylfuran-2-yl)methanol 306, which may then be converted to 2-(chloromethyl)-5-methylfuran 308, and in turn reduced to form 2,5-dimethylfuran 310.

In yet other embodiments, with reference to FIG. 3B', 5-(chloromethyl)furfural 302 may be converted to 5-methylfuran-2-carbaldehyde 304 in the presence of hydrogen, a catalyst, such as a palladium (Pd) catalyst, and an amide or urea reagent as described herein. 5-Methylfuran-2-carbaldehyde 304 may then be reacted with an acid, such as hydrochloric acid, in the presence of hydrogen and a metal catalyst, such as a palladium (Pd) catalyst, and an amide or urea reagent as described herein, to produce (5-methylfuran-2-yl)methanol 306, which may then be converted to 2-(chloromethyl)-5-methylfuran 308, and in turn reduced to form 2,5-dimethylfuran 310. In certain variations, the catalyst used in FIGS. 3B and 3B' may be the same or different. In certain variations, the amide or urea reagent used in FIG. 3B' may be the same or different.

In some embodiments, the reaction may be performed as a "one pot" reaction, in the same reaction vessel and/or without isolating, for example, 5-methylfuran-2-carbaldehyde or (5-methylfuran-2-yl)methanol as depicted in FIGS. 3A, 3A', 3B and 3B'. In other variations, 5-methylfuran-2-carbaldehyde may be isolated prior to conversion to (5-methylfuran-2-yl)methanol.

An example of a one pot reaction is provided in FIG. 3C. Thus, in one variation, with reference to FIG. 3C, 5-(chloromethyl)furfural 302 may be converted to 2,5-dimethylfuran 310 in a one pot reaction. As depicted in the exemplary scheme of FIG. 3C, this conversion may be performed in the presence of hydrogen, a palladium catalyst, and an amide or urea reagent as described herein. In another variation, this conversion may be performed in the further presence of an acid. In other variations, however, this conversion may be performed with acid generated in situ, in the presence of a palladium catalyst, hydrogen and an amide or urea reagent as described herein.

With reference to FIG. 3D, in another exemplary reaction scheme, 5-(chloromethyl)furfural 302 may be converted to 5-methylfuran-2-carbaldehyde 304 in the presence of hydrogen and a catalyst, such as a palladium catalyst. 5-Methylfuran-2-carbaldehyde 304 may in turn be reduced to form 2,5-dimethylfuran 310 in the presence of acid, such as hydrochloric acid, hydrogen, a palladium catalyst (such as palladium on carbon), and an amide or urea reagent as described herein. In other variations, however, this reduction may be performed with acid generated in situ, in the presence of hydrogen, a palladium catalyst (such as palladium chloride), activated carbon, and an amide or urea reagent as described herein.

With reference to FIG. 3E, in another exemplary reaction scheme, 5-(chloromethyl)furfural 302 may be converted to (5-methylfuran-2-yl)methanol 306, which may then be reduced to form 2,5-dimethylfuran 310 in the presence of acid, such as hydrochloric acid, hydrogen, a palladium catalyst (such as palladium on carbon), and an amide or urea reagent as described herein. In other variations, however, this reduction may be performed with acid generated in situ, in the presence of hydrogen, a palladium catalyst (such as palladium chloride), activated carbon, and an amide or urea reagent as described herein.

5-(Halomethyl)furfural 302 used in the exemplary reaction schemes depicted in FIGS. 3A-3E may be obtained from any commercially available sources or produced by any suitable methods known in the art.

Figure 4:
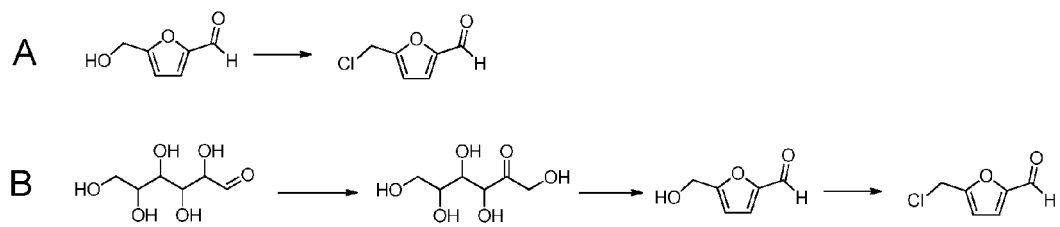
FIGS. 4A and 4B depict exemplary reaction schemes to produce 5-(chloromethyl)furfural.

In some embodiments, 5-(halomethyl)furfural may be produced from 5-(hydroxymethyl)furfural, as depicted in the exemplary reactions of FIGS. 4A and 4B. With reference to FIG. 4A, 5-(hydroxymethyl)furfural may be converted into 5-(chloromethyl)furfural in the presence of an acid. In one example, 5-(hydroxymethyl)furfural may be reacted with 10N HCl at room temperature. In another example, 5-(hydroxymethyl)furfural may be reacted with 5N $H^+$ and 11N $Cl^-$ at room temperature.

With reference to FIG. 4B, glucose may be converted to fructose in the presence of an acid and/or salt. For example, in an exemplary reaction, glucose may be converted to fructose using 1N $H^+$, 12N $Cl^-$, 11N $Li^+$, and toluene as a solvent at elevated temperatures (e.g., 110° C.). Fructose may then be converted to 5-(hydroxymethyl)furfural, which may in turn be converted to 5-(chloromethyl)furfural as described above.

Thus, provided herein are methods to produce alkylfurans from various furan compounds. For example, various furan compounds may be used to produce 2,5-dimethylfuran as shown in the exemplary reaction schemes in FIGS. 5A-5D. Such furan compounds may include, for example, 5-(halomethyl)furfural (or also referred to as 5-(halomethyl)furan-2-carbaldehyde; FIG. 5A; where Y is halo), 5-methylfuran-2-carbaldehyde (FIG. 5B), (5-methylfuran-2-yl)methanol (FIG. 5C), and 2-(halomethyl)-5-methylfuran (FIG. 5D; where X is halo).

In other examples, various furan compounds may be used to produce 2-methylfuran as shown in the exemplary reaction schemes in FIGS. 5E-5G. Such furan compounds may including, for example, furfural (or also referred to as furan-2-carbaldehyde; FIG. 5E), furan-2-ylmethanol (FIG. 5F), and 2-(halomethyl)furan (FIG. 5G; where X is halo).

Figure 6:
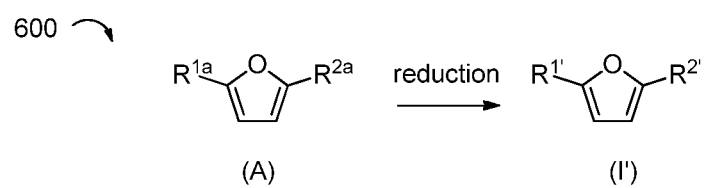
FIG. 6 depicts an exemplary reaction scheme to produce an alkylfuran having the structure of formula (I') from a compound having the structure of formula (A).

With reference in FIG. 6, in some variations, the alkylfurans are compounds having the structure of formula (I'):

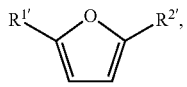

(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1.

Thus, with reference to process 600 in FIG. 6, in certain aspects, provided is a method of producing a compound of formula (I') by reducing a compound of formula (A) having the structure:

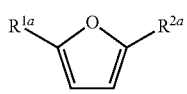

(A)

wherein:
R$^{1a}$ is C$_m$ alkyl, or —(CH$_2$)$_m$Y, wherein m is as defined for formula (I'), provided that when m is 0, R$^{1a}$ is H; and Y is halo; and
R$^{2a}$ is —(CH$_2$)$_{n-1}$CH(O), —(CH$_2$)$_n$OH, or —(CH$_2$)$_n$X, wherein n is as defined for formula (I'), and X is halo.

In one variation, the compound of formula (A) is reduced to produce the compound of formula (I') in the presence of a catalyst, and hydrogen. In another variation, the compound of formula (A) is reduced to produce the compound of formula (I') in the presence of a catalyst, hydrogen, and one or more reagents having an amide or urea moiety. In yet another variation, the compound of formula (A) is reduced to produce the compound of formula (I') in the presence of a catalyst, hydrogen, one or more reagents having an amide or urea moiety, and solvent.

The alkylfurans (e.g., the compounds of formula (I')), the furan compounds (e.g., the compounds of formula (A)), the catalysts, the acids, the hydrogen, the amine or urea reagents and the solvents, as well as the reaction conditions to produce the compounds of formula (I') are each described in further detail below.

Alkylfurans

In some aspects, the methods provided herein produce alkylfurans that are compounds having the structure of formula (I'):

(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1.

In some variations, the methods provided herein produce compounds having the structure of formula (I'), wherein m is 0, and thus R$^{1'}$ is H. Examples of such compounds include compounds of formula (I-a):

(I-a)

wherein:
R$^{2'}$ is C$_n$ alkyl, wherein n is an integer greater than or equal to 1.

Thus, in some variation, provided herein are methods of producing a compound of formula (I-a) from a compound of formula (A).

In other variations, the methods provided herein produce compounds having the structure of formula (I'), wherein R$^{1'}$ is C$_m$ alkyl, wherein m is an integer greater than or equal to 1. Examples of such compounds include compounds of formula (I-b):

(I-b)

wherein:

$R^{1'}$ is $C_m$ alkyl, wherein m is an integer greater than or equal to 1; and $R^{2'}$ is $C_n$ alkyl, wherein n is an integer greater than or equal to 1.

Thus, in some variation, provided herein are methods of producing a compound of formula (I-b) from a compound of formula (A).

In some aspects, the methods provided herein produce dialkylfurans having the structure of formula (I):

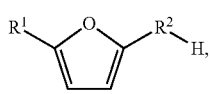
(I)

wherein:

$R^1$ is $C_m$ alkyl, wherein m is an integer greater than or equal to 1; and $R^2$ is $-(CH_2)_n-$, wherein n is an integer greater than or equal to 1.

Thus, in some variation, provided herein are methods of producing a dialkylfuran of formula (I) from a compound of formula (A).

In some variations of the compound of formula (I') or (I-a), m is 0. In other variations of the compound of formula (I'), (I) or (I-b), m is between 1 and 50, between 1 and 25, between 1 and 20, between 1 and 15, between 1 and 10, or between 1 and 5. In certain variations, m is 1, 2, 3, 4, or 5. In one variation, m is 1.

In some variations of the compound of formula (I'), (I), (I-a) or (I-b), n is between 1 and 50, between 1 and 25, between 1 and 20, between 1 and 15, between 1 and 10, or between 1 and 5. In certain variations, n is 1, 2, 3, 4, or 5. In one variation, n is 1.

In other variations of the compound of formula (I'), (I), (I-a) or (I-b), it should be understood that any combinations of variables m and n described above can be used. For example, in certain variations of the compound of formula (I') or (I), m is between 1 and 50; and n is between 1 and 50. In one variation, m is 1, and n is 2. In another variation of the compound of formula (I) or (I-a), m is 0, and n is 1. Variables m and n may, in certain embodiments, be the same integer or a different integer.

In certain embodiments, the compound of formula (I') or (I-a) may be an alkylfuran such as:

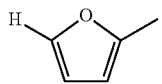

(i.e., 2-methylfuran), wherein m is 0 and n is 1.

In certain embodiments, the compound of formula (I'), (I) or (I-b) may be a dialkylfuran such as:

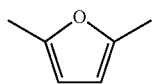

(i.e., 2,5-dimethylfuran), wherein m is 1, and n is 1; or

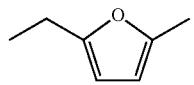

(i.e., 2-ethyl-5-methylfuran), wherein m is 2, and n is 1; or m is 1, and n is 2.

It should be understood that the methods described herein to produce the compounds of formula (I') also apply to the compounds of formula (I), (I-a) and (I-b), to the extent that is chemically feasible.

Compounds of Formula (A)

In some aspects, the methods provided herein produce compounds of formula (I') from compounds of formula (A):

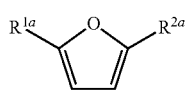
(A)

wherein:

$R^{1a}$ is $C_m$ alkyl, or $-(CH_2)_mY$, wherein:

m is an integer greater than or equal to 0, provided that when m is 0, $R^{1a}$ is H; and Y is halo; and $R^{2a}$ is $-(CH_2)_{n-1}CH(O)$, $-(CH_2)_nOH$, or $-(CH_2)_nX$, wherein:

n is an integer greater than or equal to 1; and

X is halo.

In some variations, the methods provided herein produce compounds having the structure of formula (I'), wherein m is 0, and thus $R^{1'}$ is H, from compounds of formula (A-i):

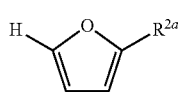
(A-i)

wherein:

$R^{2a}$ is $-(CH_2)_{n-1}CH(O)$, $-(CH_2)_nOH$, or $-(CH_2)_nX$, wherein n is as defined for formula (I'), and X is halo.

In other variations, the methods provided herein produce compounds having the structure of formula (I'), wherein $R^{1'}$ is $C_m$ alkyl, wherein m is an integer greater than or equal to 1. Examples of such compounds include compounds of formula (A-ii):

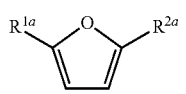
(A-ii)

wherein:

$R^{1a}$ is $C_m$ alkyl, or $-(CH_2)_mY$, wherein:

m is an integer greater than or equal to 1; and

Y is halo; and $R^{2a}$ is $-(CH_2)_{n-1}CH(O)$, $-(CH_2)_nOH$, or $-(CH_2)_nX$, wherein:

n is an integer greater than or equal to 1, and

X is halo.

In some variations of the compound of formula (A) and (A-i), $R^{1a}$ is H. Examples of such compounds include:

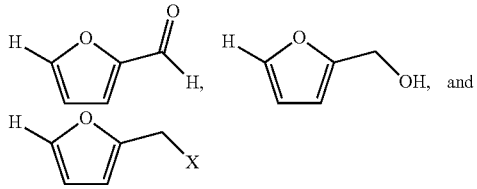

(wherein X is halo).

In other variations of the compound of formula (A) and (A-ii), $R^{1a}$ is $C_m$ alkyl. For example, in one variation, $R^{1a}$ is methyl (i.e., $C_1$ alkyl), ethyl (i.e., $C_2$ alkyl), or propyl (i.e., $C_3$ alkyl). Examples of such compounds include:

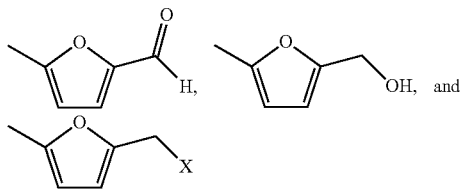

(wherein X is halo).

In yet other variations of the compound of formula (A) and (A-ii), $R^{1a}$ is $-(CH_2)_m Y$. For example, in one variation, $R^{1a}$ is $-CH_2Y$, $-CH_2CH_2Y$, or $-CH_2CH_2CH_2Y$. In one embodiment, Y is chloro. In another embodiments, Y is bromo. In yet another embodiment, Y is fluoro. Examples of such compounds include:

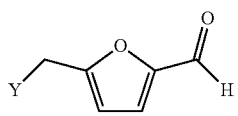

(wherein Y is halo).

In some variations of the compound of formula (A), (A-i) and (A-ii) that may be combined with any of the foregoing variations, $R^{2a}$ is $-(CH_2)_{n-1}CH(O)$. Examples of such compounds include:

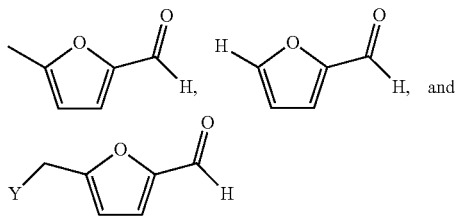

(wherein Y is halo).

In other variations of the compound of formula (A), (A-i) and (A-ii) that may be combined with any of the foregoing variations, $R^{2a}$ is $-(CH_2)_n OH$. Examples of such compounds include:

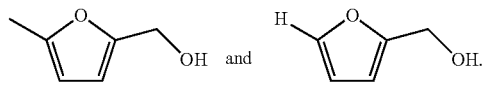

In other variations of the compound of formula (A), (A-i) and (A-ii) that may be combined with any of the foregoing variations, $R^{2a}$ is $-(CH_2)_n X$. In one embodiment, X is chloro. In another embodiments, X is bromo. In yet another embodiment, X is fluoro. Examples of such compounds include:

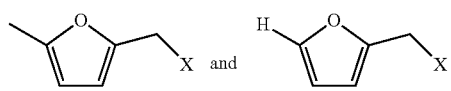

(wherein X is halo).

It should be understood that any variations of $R^{1a}$ and $R^{2a}$ may be combined as if each and every variation was individually listed. For example, with reference to FIG. 5A, the compound of formula (A) is

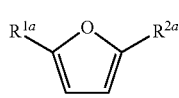

(A)

wherein:
$R^{1a}$ is $-(CH_2)_m Y$, wherein:
m is an integer greater than or equal to 1; and
Y is halo; and
$R^{2a}$ is $-(CH_2)_{n-1}CH(O)$, wherein:
n is an integer greater than or equal to 1.

In one variation, the compound of formula (A) is:

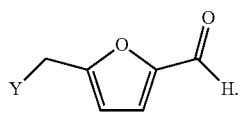

In another example, with reference to FIG. 5B, the compound of formula (A) is:

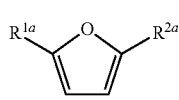

(A)

wherein:
$R^{1a}$ is $C_m$ alkyl, wherein:
m is an integer greater than or equal to 1; and
$R^{2a}$ is $-(CH_2)_{n-1}CH(O)$, wherein:
n is an integer greater than or equal to 1.

In one variation, the compound of formula (A) is:

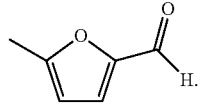

In another example, with reference to FIG. 5C, the compound of formula (A) is:

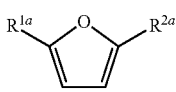
(A)

wherein:
$R^{1a}$ is $C_m$ alkyl, wherein:
m is an integer greater than or equal to 1; and
$R^{2a}$ is —$(CH_2)_n$OH, wherein:
n is an integer greater than or equal to 1.
In one variation, the compound of formula (A) is:

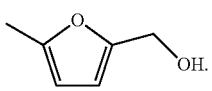

In yet another example, with reference to FIG. 5D, the compound of formula (A) is:

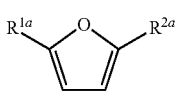
(A)

wherein:
$R^{1a}$ is $C_m$ alkyl, wherein:
m is an integer greater than or equal to 1; and
$R^{2a}$ is —$(CH_2)_n$X, wherein:
n is an integer greater than or equal to 1; and
X is halo.
In one variation, the compound of formula (A) is:

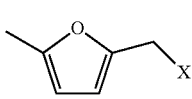

(wherein X is halo).

In another example, with reference to FIG. 5E, the compound of formula (A) is:

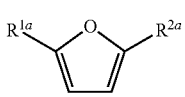
(A)

wherein:
$R^{1a}$ is H; and
$R^{2a}$ is —$(CH_2)_{n-1}$CH(O), wherein:
n is an integer greater than or equal to 1.
In one variation, the compound of formula (A) is:

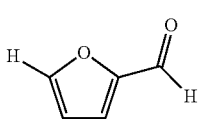

In yet another example, with reference to FIG. 5F, the compound of formula (A) is:

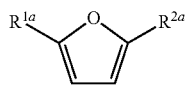
(A)

wherein:
$R^{1a}$ is H: and
$R^{2a}$ is —$(CH_2)_n$OH, wherein:
n is an integer greater than or equal to 1.
In one variation, the compound of formula (A) is:

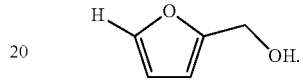

In yet another example, with reference to FIG. 5G, the compound of formula (A) is:

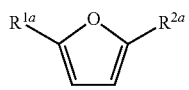
(A)

wherein:
$R^{1a}$ is H: and
$R^{2a}$ is —$(CH_2)_n$X, wherein:
n is an integer greater than or equal to 1; and
X is halo.
In one variation, the compound of formula (A) is:

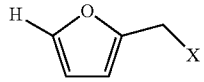

(wherein X is halo).

In some variations of the compound of formula (A) or (A-i), m is 0. In some variations of the compound of formula (A), (A-i) or (A-ii), m is between 1 and 50, between 1 and 25, between 1 and 20, between 1 and 15, between 1 and 10, or between 1 and 5. In certain variations, m is 1, 2, 3, 4, or 5. In one variation, m is 1.

In some variations of the compound of formula (A), (A-i) or (A-ii), n is between 1 and 50, between 1 and 25, between 1 and 20, between 1 and 15, between 1 and 10, or between 1 and 5. In certain variations, n is 1, 2, 3, 4, or 5. In one variation, n is 1.

In other variations of the compound of formula (A), (A-i) or (A-ii), it should be understood that any combinations of variables m and n described above can be used. For example, in certain variations of the compound of formula (I') or (I), m is between 1 and 50; and n is between 1 and 50. In one variation, m is 1, and n is 2. In another variation, m is 0, and n is 1. Variables m and n may, in certain embodiments, be the same integer or a different integer.

In certain embodiments, the compound of formula (A) or (A-i) may be:

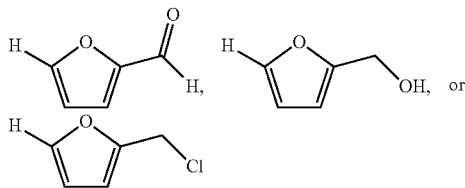

(wherein m is 0 and n is 1 in each instance).

In certain embodiments, the compound of formula (A) or (A-ii) may be:

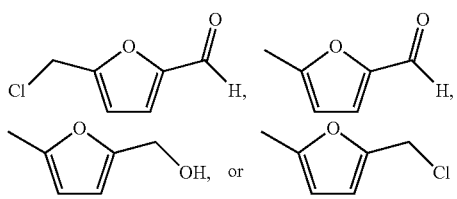

(wherein m is 1 and n is 1 in each instance).

Catalysts

In some variations of the methods provided herein to produce alkylfurans, the compounds of formula (A) may be reduced in the presence of a catalyst. The catalysts used herein may be obtained from any commercially available sources or prepared according to any suitable methods known in the art. Suitable catalysts include any catalysts that can improve selectivity of the formation of dialkylfurans and other alkylfurans, while minimizing the formation of other products.

In some embodiments, the catalyst includes palladium. Suitable catalysts may include, for example, palladium on carbon (Pd/C) or palladium chloride ($PdCl_2$).

In certain embodiments, the catalyst further includes a solid support. In other words, the catalyst may be a solid supported catalyst. Suitable supports may include, for example, carbon, and alumina ($Al_2O_3$). For example, in some variations, the catalyst includes palladium supported on carbon or alumina ($Al_2O_3$). In one variation, the catalyst is palladium on carbon (Pd/C) or palladium on alumina (Pd/alumina).

Acid

In some variations of the methods provided herein to produce alkylfurans, the compounds of formula (A) may be reduced in the further presence of acid. Suitable acids may include acids having the formula H—X, where X is halo. In one variation where the acid is H—X, X is chloro. In another variation, X is bromo. In yet another variation, X is fluoro. In other variations, the acid is a solid acid.

Such acid may be added to the reaction mixture or generated in situ from the catalysts described herein. For example, in one variation, hydrochloric acid may be generated in situ in the reaction mixture from 5-(chloromethyl) furfural in the presence of hydrogen. In other variations, hydrochloric acid may be generated in situ in the reaction mixture from 5-(chloromethyl)furfural in the presence of a catalyst and/or carbon (e.g., activated carbon).

The amounts of acid present in the reaction mixture may vary based on the compound of formula (A), the catalyst, the amount of hydrogen, and the amine or urea reagent. In certain variations, the amount of acid present in the reaction mixture does not exceed an amount that would decrease the activity of the catalyst.

In other variations, the amount of acid present in the reaction mixture is an amount that results in a yield of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, with respect to the compound of formula (I), (I'), (I-a) or (I-b).

Amide and Urea Reagents

In some variations of the methods provided herein to produce alkylfurans, the compounds of formula (A) may be reduced in the presence of a reagent that has an amide or urea moiety. The reagents described herein may, under certain conditions, also act as a solvent.

In some embodiments, the reagent is a compound of formula (i):

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms.

In some variations of the reagent of formula (i), each $R^a$, $R^b$ and $R^c$ is independently H, alkyl, aryl, or heteroaryl. In certain variations, each $R^a$ and $R^b$ is independently alkyl. In one variation, each $R^a$ and $R^b$ is independently $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In yet other variations, $R^c$ is alkyl, aryl or heteroaryl. In certain variations, the reagent of formula (i) is other than N,N-dimethylformamide and N,N-dimethylacetamide. In other variations of the reagent of formula (i), when $R^c$ is H or methyl, then one of $R^a$ and $R^b$ is other than methyl.

In other embodiments, the reagent is a compound of formula (ii):

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

In some variations of the reagent of formula (ii), each $R^a$, $R^b$ and $R^c$ is independently H, alkyl, aryl, or heteroaryl. In certain variations, each $R^a$ and $R^b$ is independently alkyl. In one variation, each $R^a$ and $R^b$ is independently $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In some variations of the reagent of formula (ii), $R^a$ and $R^b$ are taken together with the nitrogen atoms to which they are connected to form a cyclic moiety having at least 4, or at least 5, or between 3 and 20, or between 3 and 15, or between 4 and 20, or between 4 and 15, or between 4 and 10, or between 4 and 8 ring atoms.

In some variations of the reagent of formula (ii), $R^c$ and $R^d$ are taken together with the nitrogen atoms to which they are connected to form a cyclic moiety having at least 4, or at least 5, or between 3 and 20, or between 3 and 15, or between 4 and 20, or between 4 and 15, or between 4 and 10, or between 4 and 8 ring atoms.

In some variations of the reagent of formula (ii), $R^b$ and $R^d$ are taken together with the nitrogen atoms to which they are connected to form a cyclic moiety having at least 6, or at least 7, or between 6 and 20, or between 6 and 15, or between 7 and 20, or between 7 and 15, or between 7 and 10 ring atoms.

In some variations of the reagent of formula (ii), $R^a$ and $R^c$ are taken together with the nitrogen atoms to which they are connected to form a cyclic moiety having at least 6, or at least 7, or between 6 and 20, or between 6 and 15, or between 7 and 20, or between 7 and 15, or between 7 and 10 ring atoms.

In other embodiments, the reagent is a compound of formula (iii):

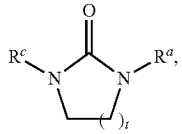

(iii)

wherein:
each $R^a$ and $R^c$ is independently H, aliphatic, aryl or heteroaryl; and
t is an integer greater than or equal to 0, In some variations of the reagent of formula (iii), each $R^a$ and $R^c$ is independently H, alkyl, aryl, or heteroaryl. In certain variations, $R^a$ is alkyl. In one variation, $R^a$ is $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In some variations of the reagent of formula (iii), t is an integer greater than or equal to 1. In certain variations, t is an integer between 1 and 12, between 1 and 10, between 1 and 9, between 1 and 8, between 1 and 7, between 1 and 6, or 5, 4, 3, 2 or 1.

In some embodiments of the methods described herein, exemplary amide or urea reagents suitable for use in the methods provided herein include:

In other variations, the reagent is

-continued

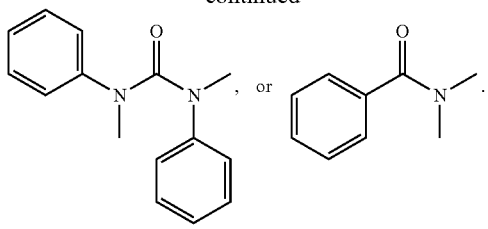

In one variation, the reagent is:

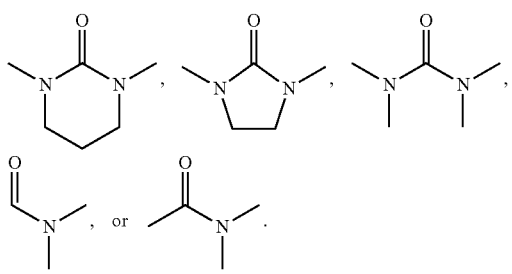

In yet another variation, the reagent is:

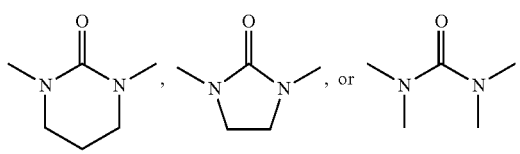

Any combination of the reagents described herein, including the reagents having the formula (i), (ii) and (iii), and the specific examples of reagents described above, may also be used.

Hydrogen

In some embodiments, the compound of formula (A) is reduced to produce the compound of formula (I'), (I), (I-a) or (I-b) in the presence of hydrogen. The hydrogen may be provided in the form of hydrogen gas or by transfer hydrogenation (e.g., by addition of cyclohexene or cyclohexadiene to the reaction mixture as the hydrogen source).

In certain variations, the compound of formula (A) is reduced to produce the compound of formula (I'), (I), (I-a) or (I-b) in the presence of hydrogen gas. In one variation, the compound of formula (A) is reduced at a pressure of at least 1 psi, or at least 10 psi; or between 1 psi and 1500 psi, between 1 psi and 1000 psi, between 500 psi to 1500 psi, between 1 psi and 50 psi, between 1 psi and 100 psi, between 1 psi and 80 psi, between 1 psi and 75 psi, or between 30 psi and 60 psi. It should be understood that the hydrogen gas may be dissolved, or at least partially dissolved, in the reagents and/or other solvents described herein.

Solvent

In some embodiments, the compound of formula (A) is reduced to produce the compound of formula (I'), (I), (I-a) or (I-b) in the presence of solvent. The solvents used may be obtained from any source, including any commercially available source.

In certain embodiments, the solvent includes organic solvent. Suitable organic solvents may include, for example, aromatic solvents. In some variations, the solvent includes at least one mono-aryl compound, at least one di-aryl compound, or at least one tri-aryl compound, or any mixtures thereof. In one variation, the solvent includes toluene or para-xylene. Any combinations or mixture of the solvents described herein may also be used.

In other embodiments, as discussed above, the reagents of formula (i), (ii) and (iii), or any combinations thereof, may act as a solvent. Thus, in one variation, no additional solvent is added where the reagents of formula (i), (ii) and (iii), or any combinations thereof, are used. In another variation, the compound of formula (A) is reduced to produce the compound of formula (I'), (I), (I-a) or (I-b) in the presence of a reagent of formula (i), (ii) or (iii), or any combinations thereof, and any of the other solvents described herein.

Reaction Conditions

The operating temperature refers to the average temperature of the reaction mixture in the vessel. In some embodiments, the operating temperature may be at least 10° C., at least 15° C., at least 25° C., at least 100° C., or at least 150° C.; or between 0° C. and 250° C., between 0° C. and 200° C., between 0° C. and 150° C., between 0° C. and 100° C., between 5° C. and 80° C., or between 10° C. and 75° C., between 15° C. and 65° C., or between 130° C. and 250° C.

The operating pressure refers to the average absolute internal pressure of the vessel. In some embodiments, the operating pressure may be at least 1 psi, or at least 10 psi; or between 1 psi and 1500 psi, between 1 psi and 1000 psi, between 500 psi to 1500 psi, between 1 psi and 50 psi, between 1 psi and 100 psi, between 1 psi and 80 psi, between 1 psi and 75 psi, or between 30 psi and 60 psi.

It should be understood that temperature may be expressed as degrees Celsius (° C.) or Kelvin (K). One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). One of ordinary skill in the art would be able to convert the pressure described herein from one unit to another.

The method (e.g., the reduction of the compound of formula (A) to the compound of formula (I)) may be performed with or without stirring. In certain embodiments, the method (e.g., the reduction of the compound of formula (A) to the compound of formula (I'), (I), (I-a) and (I-b)) is performed with stirring to increase conversion and/or selectivity.

Additionally, the methods described herein may be carried out batch-wise or continuously. The reaction time (in a batch-wise process) or residence time (in a continuous process) will also vary with the reaction conditions and desired yield, but is generally about 1 to 72 hours. In some of the foregoing embodiments, the reaction time or residence time is determined by the rate of conversion of the starting material. In some of the foregoing embodiments, the reaction mixture is reacted for 1 to 24 hours. In some of the foregoing embodiments, the reaction mixture is reacted for 1 to 10 hours. In some of the foregoing embodiments, the reaction mixture is reacted for 1 to 5 hours. In some of the foregoing embodiments, the reaction mixture is reacted for 1 to 3 hours. In some of the foregoing embodiments, the reaction mixture is reacted for less than 2 hours, less than 1 hour, less than 30 minutes, less than 10 minutes, or less than 5 minutes.

Isolation and Purification

The methods described herein may further include isolating and/or purifying the alkylfurans, e.g., the compounds of formula (I'), (I), (I-a) and (I-b), from the reaction mixture. Any methods known in the art may be employed to isolate and/or purify the alkylfurans. For example, the alkylfurans, e.g., the compounds of formula (I'), (I), (I-a) and (I-b), may be isolated and/or purified by distillation. In another example, the alkylfurans, e.g., the compounds of formula (I'), (I), (I-a) and (I-b), may be isolated by distillation, and the isolated alkylfuran may be further purified by chromatography.

It should be understood that in certain variations, the alkylfuran produced is not isolated and/or purified, and may be further used in one or more downstream reactions described herein (e.g., to produce para-xylene and/or terephthalic acid).

Yield, Conversion and Selectivity

The yield of a product takes into account the conversion of the starting materials into the product, and the selectivity for the product over other products that may be formed.

The difference between yield, conversion and selectivity is explained in the examples provided below. For example, with respect to the conversion of a compound of formula (A) into a compound of formula (I'), (I), (I-a) or (I-b), the reaction can be generalized as follows, where "A" represents the moles of the compound of formula (A); and "C" represents the moles of the compound of formula (I'), (I), (I-a) or (I-b); and "a" and "c" are stoichiometric coefficients.

$$aA \rightarrow cC$$

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the stoichiometrically relative amount of product C produced from the converted amount of reactant A, as expressed as a percentage by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C. In some embodiments where "a/c"=1, and the equation can be simplified to:

$$\text{Selectivity (\%)} = \frac{Cf}{Ao - Af} * 100\%.$$

The yield of product C is the percentage of reactant A that is converted into product C, as expressed by the following equation:

Yield (%)=Conversion (%)*Selectivity (%)

In certain embodiments, the methods described herein have a yield of at least 10%, at least 15%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 15% to 100%, between 15% to 90%, between 20% to 80%, between 30% to 80%, between 40% to 80%, between 50%-80%, or between 60%-80% by weight.

In certain embodiments, the methods described herein have a selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Downstream Products

The compounds of formula (I'), (I), (I-a) and (I-b), such as 2,5-dimethylfuran and 2-methylfuran, produced according to the methods described herein may be suitable for manufacture of one or more plastics, fuels (e.g., transportation fuels) or other compounds. For example, 2,5-dimethylfuran may be converted to para-xylene. See e.g., U.S. 2013/0245316.

Thus, in some aspects, provided is a method of producing para-xylene, by combining 2,5-dimethylfuran produced according to any of the methods described herein and ethylene to produce para-xylene. In other aspects, provided is a method of producing terephthalic acid by: combining 2,5-dimethylfuran produced according to any of the methods described herein and ethylene to produce para-xylene; and oxidizing the para-xylene to terephthalic acid. In yet other aspects, provided is a method of producing polyethylene terephthalate by: combining 2,5-dimethylfuran produced according to any of the methods described herein and ethylene to produce para-xylene; oxidizing the para-xylene to terephthalic acid; and polymerizing terephthalic acid with ethylene glycol to yield polyethylene terephthalate using any methods known in the art.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

It should also be understood that reference to "between" two values or parameters herein includes (and describes) embodiments that include those two values or parameters per se. For example, description referring to "between x and y" includes description of "x" and "y" per se.

As used herein, "aliphatic" refers to a monoradical unbranched or branched hydrocarbon chain that may be saturated (e.g., alkyl) or unsaturated (e.g., alkenyl or alkynyl). In some embodiments, aliphatic as used herein, such as in reagents of formula (i), (ii) and (iii), has 1 to 20 carbon atoms (i.e., $C_{1-20}$ aliphatic), 1 to 8 carbon atoms (i.e., $C_{1-8}$ aliphatic), 1 to 6 carbon atoms (i.e., $C_{1-6}$ aliphatic), or 1 to 4 carbon atoms (i.e., $C_{1-4}$ aliphatic).

"Alkyl" refers to a monoradical unbranched or branched saturated hydrocarbon chain. In some embodiments, alkyl as used herein, such as in compounds of formula (I') (including, for example, formula (I), formula (I-a) and formula (I-b)) and formula (A) (including, for example, formula (A-i) and (A-ii)), has 1 to 50 carbon atoms (i.e., $C_{1-50}$ alkyl), 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl.

"Aryl" refers to an aromatic carbocyclic group having a single ring (e.g., phenyl), multiple rings (e.g., biphenyl), or multiple fused rings (e.g., naphthyl, fluorenyl, and anthryl), in certain embodiments, aryl as used herein, such as in compounds of formula (A) (including, for example, formula (A-i) and (A-ii)), has 6 to 50 ring carbon atoms (i.e., $C_{6-50}$ aryl), 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein, such as in compounds of formula (A) (including, for example, formula (A-i) and (A-ii)), has 3 to 50 ring carbon atoms (i.e., $C_{3-50}$ heteroaryl), 3 to 20 ring carbon atoms (i.e., $C_{3-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl as defined above.

Further, it should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

ENUMERATED EMBODIMENTS

The following enumerated embodiments are representative of some aspects of the invention.
1. A method of producing 2,5-dimethylfuran, comprising:
   a) providing (5-methylfuran-2-yl)methanol; and
   b) selectively reducing the (5-methylfuran-2-yl)methanol to produce 2,5-dimethylfuran.
2. The method of embodiment 1, wherein the (5-methylfuran-2-yl)methanol is selectively reduced in the presence of hydrogen and a catalyst.
3. A method of producing 2,5-dimethylfuran, comprising:
   a) providing (5-methylfuran-2-yl)methanol;
   b) converting the (5-methylfuran-2-yl)methanol to 2-(chloromethyl)-5-methylfuran in the presence of an acid; and
   c) selectively reducing the 2-(chloromethyl)-5-methylfuran to produce 2,5-dimethylfuran.
4. The method of embodiment 3, wherein the 2-(chloromethyl)-5-methylfuran is selectively reduced in the presence of hydrogen and a catalyst.
5. The method of any one of embodiments 1 to 6, wherein the (5-methylfuran-2-yl)methanol is provided by:
   i) providing 5-methylfuran-2-carbaldehyde; and
   ii) converting the 5-methylfuran-2-carbaldehyde to (5-methylfuran-2-yl)methanol in the presence of acid, hydrogen and a catalyst.
6. The method of any one of embodiments 1 to 6, wherein the (5-methylfuran-2-yl)methanol is provided by:
   i) providing 5-(chloromethyl)furfural;
   ii) converting the 5-(chloromethyl)furfural to 5-methylfuran-2-carbaldehyde in the presence of hydrogen and a catalyst; and
   iii) converting the 5-methylfuran-2-carbaldehyde in the presence of acid, hydrogen and a catalyst.
7. The method of embodiment 2, 4, 5 or 6, wherein the catalyst is a palladium catalyst.
8. A method of producing a compound of formula (I'):

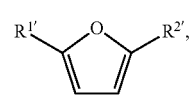

(I')

wherein:
   $R^{1'}$ is $C_m$ alkyl, wherein m is an integer greater than or equal to 0, provided that when m is 0, $R^{1'}$ is H; and
   $R^{2'}$ is $C_n$ alkyl, wherein n is an integer greater than or equal to 1,
the method comprising converting a compound of formula (A) to the compound of formula (I') in the presence of hydrogen, a catalyst and a reagent of formula (i), (ii) or (iii), or any combination thereof,
wherein:
   the compound of formula (A) is:

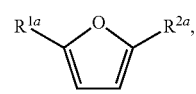

(A)

wherein:
   $R^{1a}$ is $C_m$ alkyl, or —$(CH_2)_m$Y, wherein:
      m is as defined for formula (I'), provided that when m is 0, $R^{1a}$ is H; and
      Y is halo; and
   $R^{2a}$ is —$(CH_2)_{n-1}$CH(O), —$(CH_2)_n$OH, or —$(CH_2)_n$X, wherein:
      n is as defined for formula (I'); and
      X is halo; and
the reagent of formula (i) is:

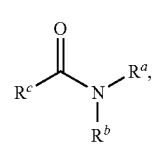

(i)

wherein:
  each $R^a$, $R^b$ and $R^c$ is independently H, aliphatic, aryl, or heteroaryl; or
  $R^a$ and $R^b$ are taken together with the nitrogen atoms to which they are connected to form a cyclic moiety having at least 3 ring atoms; and
the reagent of formula (ii) is:

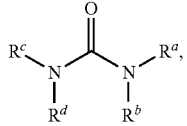

(ii)

wherein:
  (A) each $R^a$, $R^b$, $R^c$ and $R^d$ is independently H, aliphatic, aryl or heteroaryl; or
  (B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
  (C) each $R^a$ and $R^b$ is independently H, aliphatic, aryl or heteroaryl;
  and $R^c$ and $R^d$ are taken together with the nitrogen atoms to which they are connected to form a cyclic moiety having at least 3 ring atoms; or
  (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
  (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
  (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and the reagent of formula (iii) is:

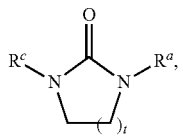

(iii)

wherein:
  each $R^a$ and $R^c$ is independently H, aliphatic, aryl or heteroaryl; and
  t is an integer greater than or equal to 0.

9. The method of embodiment 8, wherein:
  the reagent of formula (i) is other than N,N-dimethylformamide and N,N-dimethylacetamide; or
  the reagent is a reagent of formula (i), provided that when $R^c$ is H or methyl, then one of $R^a$ and $R^b$ is other than methyl.

10. The method of embodiment 8, wherein the reagent of formula (i), (ii) or (iii) is selected from the group consisting of

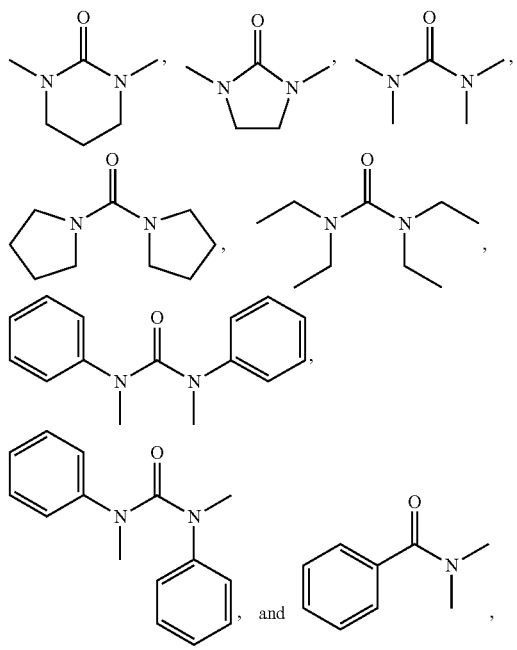

or any combinations thereof.

11. The method of any one of embodiments 8 to 10, wherein the compound of formula (I') is a compound of formula (I-a) or (I-b):

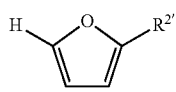

(I-a)

or

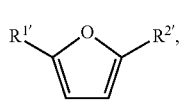

(I-b)

wherein $R^{1'}$ is $C_m$ alkyl, wherein m is an integer greater than or equal to 1.

12. The method of embodiment 8, wherein the compound of formula (I') is

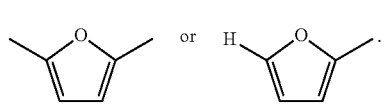

13. The method of embodiment 8 or 9, wherein the compound of formula (A) is a compound of formula (A-i) or (A-ii):

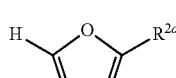

(A-i)

or

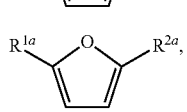

(A-ii)

wherein m is an integer greater than or equal to 1.

14. The method of any one of embodiments 8 to 11 and 13, wherein $R^{1a}$ is —$(CH_2)_m Y$.
15. The method of any one of embodiments 8 to 13, wherein $R^{2a}$ is —$(CH_2)_{n-1}CH(O)$.
16. The method of any one of embodiments 8 to 13, wherein $R^{2a}$ is —$(CH_2)_n OH$.
17. The method of any one of embodiments 8 to 13, wherein $R^{2a}$ is —$(CH_2)_n X$.
18. The method of any one of embodiments 8 to 11, wherein the compound of formula (A) is

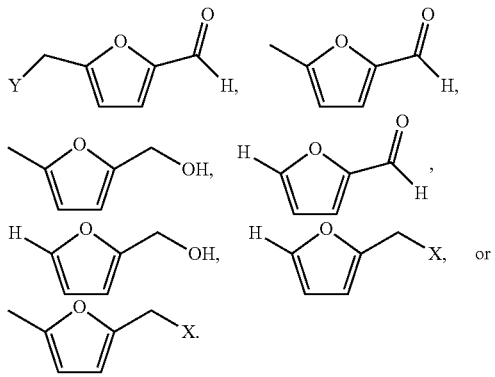

19. The method of embodiment 8, wherein the compound of formula (A) is

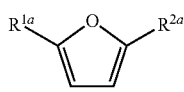

wherein:
  $R^{1a}$ is —$(CH_2)_m Y$, wherein:
    m is an integer greater than or equal to 1; and
    Y is halo; and
  $R^{2a}$ is —$(CH_2)_{n-1}CH(O)$, wherein:
    n is an integer greater than or equal to 1.
20. The method of embodiment 8, wherein the compound of formula (A) is:

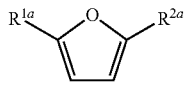

wherein:
  $R^{1a}$ is $C_m$ alkyl, wherein:
    m is an integer greater than or equal to 1; and
  $R^{2a}$ is —$(CH_2)_{n-1}CH(O)$, wherein:
    n is an integer greater than or equal to 1.
21. The method of embodiment 8, wherein the compound of formula (A) is:

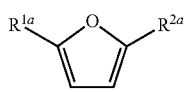

wherein:
  $R^{1a}$ is $C_m$ alkyl, wherein:
    m is an integer greater than or equal to 1; and
  $R^{2a}$ is —$(CH_2)_n OH$, wherein:
    n is an integer greater than or equal to 1.
22. The method of embodiment 8, wherein the compound of formula (A) is:

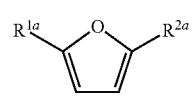

wherein:
  $R^{1a}$ is H; and
  $R^{2a}$ is —$(CH_2)_{n-1}CH(O)$, wherein:
    n is an integer greater than or equal to 1.
23. The method of embodiment 8, wherein the compound of formula (A) is:

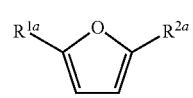

wherein:
  $R^{1a}$ is H: and
  $R^{2a}$ is —$(CH_2)_n OH$, wherein:
    n is an integer greater than or equal to 1.
24. The method of embodiment 8, wherein the compound of formula (A) is:

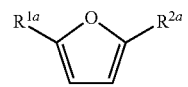

wherein:
  $R^{1a}$ is H: and
  $R^{2a}$ is —$(CH_2)_n X$, wherein:
    n is an integer greater than or equal to 1; and
    X is halo.
25. The method of embodiment 8, wherein the compound of formula (A) is:

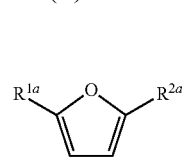

wherein:
  $R^{1a}$ is $C_m$ alkyl, wherein:
    m is an integer greater than or equal to 1; and
  $R^{2a}$ is —$(CH_2)_n X$, wherein:
    n is an integer greater than or equal to 1; and
    X is halo.
26. The method of any one of embodiments 8 to 11, 13, 14, and 18 to 25, wherein Y is chloro.
27. The method of any one of embodiments 8 to 11, 13, 17, and 18 to 25, wherein X is chloro.
28. The method of any one of embodiments 1 to 20, 22, and 24 to 27, wherein the catalyst comprises palladium.

29. The method of any one of embodiments 1 to 20, 22, and 24 to 28, wherein the catalyst comprises palladium and a solid support.
30. The method of embodiment 29, wherein the solid support is carbon or alumina.
31. The method of any one of embodiments 8 to 30, wherein the catalyst is palladium on carbon, palladium chloride, or any combinations thereof.
32. The method of any one of embodiments 8 to 31, wherein the compound of formula (A) is converted to the compound of formula (I') in the further presence of acid.
33. The method of any one of embodiments 8 to 32, wherein the compound of formula (A) is converted to the compound of formula (I') in the further presence of solvent.
34. The method of embodiment 33, wherein the solvent comprises organic solvent.
35. The method of embodiment 33 or 34, wherein the solvent comprises aromatic solvent.
36. The method of any one of embodiments 33 to 35, wherein the solvent comprises at least one mono-aryl compound, at least one di-aryl compound, or at least one tri-aryl compound, or any mixtures thereof.
37. The method of embodiment 37, wherein the at least one mono-aryl compound is toluene or para-xylene.
38. A method of producing a compound of formula (I'):

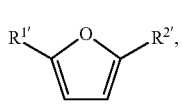
(I')

wherein:
$R^{1'}$ is $C_m$ alkyl, wherein m is an integer greater than or equal to 0, provided that when m is 0, $R^{1'}$ is H; and
$R^{2'}$ is $C_n$ alkyl, wherein n is an integer greater than or equal to 1,
the method comprising:
a) converting a compound of formula (B) to a compound of formula (C), wherein:
the compound of formula (B) is:

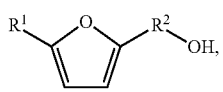
(B)

wherein:
$R^1$ is $C_m$ alkyl, wherein m is as defined for formula (I'); and
$R^2$ is —$(CH_2)_n$—, wherein n is as defined for formula (I'),
the compound of formula (C) is:

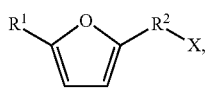
(C)

wherein:
$R^1$ and $R^2$ are as defined for formula (B); and
X is halo; and
b) reducing the compound of formula (C) to produce the compound of formula (I').

39. The method of embodiment 38, wherein the compound of formula (C) is reduced to produce the compound of formula (I') in the presence of hydrogen, a catalyst, and a reagent of formula (i), (ii) and (iii), or any combinations thereof,
wherein:
the reagent of formula (i) is:

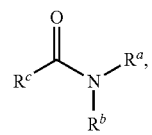
(i)

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms; and
the reagent of formula (ii) is:

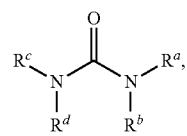
(ii)

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and the reagent of formula (iii) is:

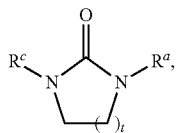

wherein:
each $R^a$ and $R^c$ is independently H, aliphatic, aryl or heteroaryl; and
t is an integer greater than or equal to 0.
40. The method of embodiment 39, wherein the reagent of formula (i), (ii) or (iii) is selected from the group consisting of

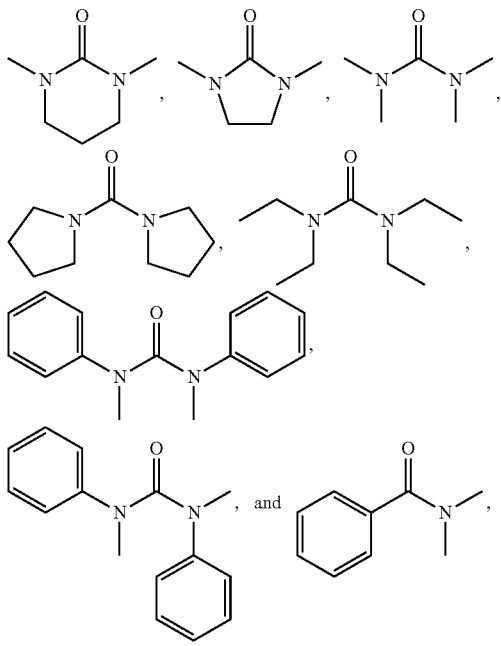

or any combinations thereof.
41. The method of embodiment 39 or 40, wherein the catalyst comprises palladium and optionally a solid support.
42. The method of embodiment 41, wherein the solid support is carbon or alumina.
43. The method of any one of embodiments 39 to 42, wherein the catalyst is palladium on carbon, palladium chloride, or any combinations thereof.
44. The method of any one of embodiments 39 to 43, wherein the compound of formula (C) is reduced to produce the compound of formula (I') in the further presence of acid.
45. The method of any one of embodiments 39 to 44, wherein the compound of formula (C) is reduced to produce the compound of formula (I') in the further presence of solvent.
46. The method of embodiment 45, wherein the solvent comprises organic solvent.
47. The method of embodiment 45 or 46, wherein the solvent comprises aromatic solvent.
48. The method of any one of embodiments 45 to 47, wherein the solvent comprises at least one mono-aryl compound, at least one di-aryl compound, or at least one tri-aryl compound, or any mixtures thereof.
49. The method of embodiment 48, wherein the at least one mono-aryl compound is toluene or para-xylene.
50. A composition, comprising:
a compound of formula (A):

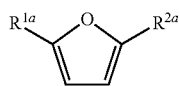

wherein:
$R^{1a}$ is $C_m$ alkyl, or $-(CH_2)_m Y$, wherein:
m is an integer greater than or equal to 0, provided that when m is 0, $R^{1'}$ is H; and
Y is halo; and
$R^{2a}$ is $-(CH_2)_{n-1}CH(O)$, $-(CH_2)_n OH$, or $-(CH_2)_n X$, wherein:
m is an integer greater than or equal to 1; and
X is halo; and
a reagent of formula (i), (ii) or (iii), or any combinations thereof, wherein:
the reagent of formula (i) is:

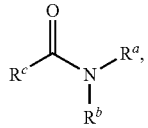

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms; and
the reagent of formula (ii) is:

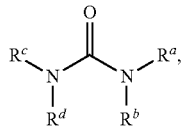

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and the reagent of formula (iii) is:

(iii)

wherein:
  each $R^a$ and $R^c$ is independently H, aliphatic, aryl or heteroaryl; and
  t is an integer greater than or equal to 0;

hydrogen; and a catalyst.

51. The composition of embodiment 50, wherein the reagent of formula (i), (ii) or (iii) is selected from the group consisting of or any combinations thereof.

52. The composition of embodiment 50 or 51, further comprising a compound of formula (I'):

(I')

wherein $R^{1'}$ and $R^{2'}$ are as defined for formula (A).

53. The composition of embodiment 51, wherein the compound of formula (I') is a compound of formula (I-a) or (I-b):

(I-a)

or (I-b)

wherein $R^{1'}$ is $C_m$ alkyl, wherein m is an integer greater than or equal to 1.

54. The composition of embodiment 51, wherein the compound of formula (I') is or

.

55. The composition of any one of embodiments 50 to 52, wherein the compound of formula (A) is a compound of formula (A-i) or (A-ii):

(A-i)

or (A-ii)

wherein m is an integer greater than or equal to 1.

56. The composition of any one of embodiments 50 to 53 and 55, wherein $R^{1a}$ is —$(CH_2)_m Y$.

57. The composition of any one of embodiments 50 to 55, wherein $R^{2a}$ is —$(CH_2)_{n-1}CH(O)$.

58. The composition of any one of embodiments 50 to 55, wherein $R^{2a}$ is —$(CH_2)_n OH$.

59. The composition of any one of embodiments 50 to 55, wherein $R^{2a}$ is —$(CH_2)_n X$.

60. The composition of any one of embodiments 50 to 53, wherein the compound of formula (A) is -continued

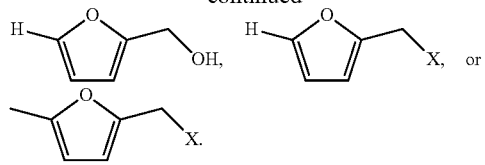

61. The composition of embodiment 50, wherein the compound of formula (A) is

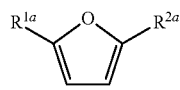

wherein:
  $R^{1a}$ is —$(CH_2)_m Y$, wherein:
    m is an integer greater than or equal to 1; and
    Y is halo; and
  $R^{2a}$ is —$(CH_2)_{n-1}CH(O)$, wherein:
    n is an integer greater than or equal to 1.

62. The composition of embodiment 50, wherein the compound of formula (A) is:

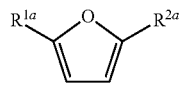

wherein:
  $R^{1a}$ is $C_m$ alkyl, wherein:
    m is an integer greater than or equal to 1; and
  $R^{2a}$ is —$(CH_2)_{n-1}CH(O)$, wherein:
    n is an integer greater than or equal to 1.

63. The composition of embodiment 50, wherein the compound of formula (A) is:

wherein:
  $R^{1a}$ is $C_m$ alkyl, wherein:
    m is an integer greater than or equal to 1; and
  $R^{2a}$ is —$(CH_2)_n OH$, wherein:
    n is an integer greater than or equal to 1.

64. The composition of embodiment 50, wherein the compound of formula (A) is:

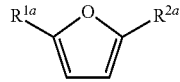

wherein:
  $R^{1a}$ is H; and
  $R^{2a}$ is —$(CH_2)_{n-1}CH(O)$, wherein:
    n is an integer greater than or equal to 1.

65. The composition of embodiment 50, wherein the compound of formula (A) is:

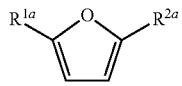

wherein:
  $R^{1a}$ is H: and
  $R^{2a}$ is —$(CH_2)_n OH$, wherein:
    n is an integer greater than or equal to 1.

66. The composition of embodiment 50, wherein the compound of formula (A) is:

wherein:
  $R^{1a}$ is H: and
  $R^{2a}$ is —$(CH_2)_n X$, wherein:
    n is an integer greater than or equal to 1; and
    X is halo.

67. The composition of embodiment 50, wherein the compound of formula (A) is:

wherein:
  $R^{1a}$ is $C_m$ alkyl, wherein:
    m is an integer greater than or equal to 1; and
  $R^{2a}$ is —$(CH_2)_n X$, wherein:
    n is an integer greater than or equal to 1; and
    X is halo.

68. The composition of any one of embodiments 50 to 53, 55, 56, and 60 to 67, wherein Y is chloro.

69. The composition of any one of embodiments 50 to 53, 55, 59, and 60 to 67, wherein X is chloro.

70. The composition of any one of embodiments 50 to 62, 64, and 66 to 69, wherein the catalyst comprises palladium.

71. The composition of any one of embodiments 50 to 62, 64, and 66 to 70, wherein the catalyst comprises palladium and a solid support.

72. The composition of embodiment 71, wherein the solid support is carbon or alumina.

73. The composition of any one of embodiments 50 to 72, wherein the catalyst is palladium on carbon, palladium chloride, or any combinations thereof.

74. The composition of any one of embodiments 50 to 73, wherein the compound of formula (A) is converted to the compound of formula (I') in the further presence of acid.

75. The composition of any one of embodiments 50 to 74, wherein the compound of formula (A) is converted to the compound of formula (I') in the further presence of solvent.

76. The composition of embodiment 75, wherein the solvent comprises organic solvent.

77. The composition of embodiment 75 or 76, wherein the solvent comprises aromatic solvent.

78. The composition of any one of embodiments 75 to 77, wherein the solvent comprises at least one mono-aryl compound, at least one di-aryl compound, or at least one tri-aryl compound, or any mixtures thereof.
79. The composition of embodiment 78, wherein the at least one mono-aryl compound is toluene or para-xylene.
80. The method of any one of embodiments 8 to 49, further comprising isolating the compound of formula (I').
81. The method of any one of embodiments 8 to 49, further comprising purifying the compound of formula (I').
82. A method of producing para-xylene, comprising:
combining a compound of formula (I') produced according to the method of any one of embodiments 8 to 49 and ethylene to produce para-xylene, wherein the compound of formula (I') is 2,5-dimethylfuran.
83. A method of producing terephthalic acid, comprising:
combining a compound of formula (I') produced according to the method of any one of embodiments 8 to 49 and ethylene to produce para-xylene, wherein the compound of formula (I') is 2,5-dimethylfuran; and
oxidizing the para-xylene to terephthalic acid.
84. A method of producing polyethylene terephthalate, comprising:
combining a compound of formula (I') produced according to the method of any one of embodiments 8 to 49 and ethylene to produce para-xylene, wherein the compound of formula (I') is 2,5-dimethylfuran;
oxidizing the para-xylene to terephthalic acid; and
polymerizing terephthalic acid with ethylene glycol to produce polyethylene terephthalate.

EXAMPLES

The following Examples are merely illustrative and are not meant to limit any aspects of the present disclosure in any way.

Example 1

Synthesis of 2,5-dimethylfuran (DMF) from 5-(chloromethyl)furfural (CMF)

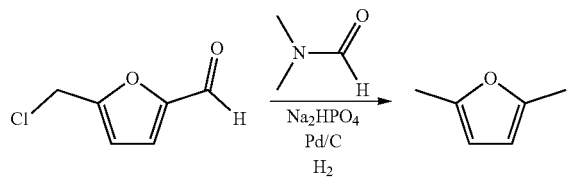

Reaction No. 1:

In a 250 mL Parr container (cooled to room temperature) was added 22.5 mL of N,N-dimethylformamide (DMFD) and $Na_2HPO_4$ (0.51 eq, 17.802 mmol, 2.5272 g). To 502 mg of 10% Pd/C was added 1 ml of DMFD and the wet paste was stirred for 1 min with a spatula. The synthesized wet paste was then added to the reaction flask under air. The remaining Pd/C paste in the vial was washed with 1.5 ml of DMFD. The reaction was then preheated to 35° C. (23 min, max T reached 42° C.) under shaking and argon (purge line connected to Argon line). CMF (5 g, 34.587 mmol) was added and the reaction was first stirred 2 min and then charged with $H_2$ up to 50 psi (charged and purged 4 times to 20 psi). The flask was refilled to 50 psi when the pressure was observed to drop to 40 psi. When $H_2$ was charged, a leak was observed. $H_2$ was flushed and Argon was added while a screw was tightened. 2 g of $Na_2HPO_4$ was added under argon after purging with $H_2$. After about 80 minutes, the reaction mixture was diluted to 100 ml with acetone and an aliquot was taken for analysis by GCMS coupled with FID. Selectivity from CMF to DMF: 79%; Yield from CMF to DMF: 72%.

Reaction No. 2:

In a 250 mL Parr container (cooled to room temperature) was added 5.0058 g (34.628 mmol) of CMF followed by 25 mL of DMFD, $Na_2HPO_4$ (0.6 eq, 20.76 mmol, 2.9471 g) and under Argon 502 mg of 10% Pd/C. The reaction flask was then preheated to 35° C. (30 min, max T reached 45° C.) under shaking and Argon (purge line connected to Argon line). The reaction was then charged with $H_2$ up to 50 psi (charged and purged 4 times to 20 psi). The flask was refilled to 50 psi every time the pressure dropped to 40 psi. After about 142 minutes, the reaction mixture was diluted to 100 ml with acetone and an aliquot was taken for analysis by GCMS coupled with FID. Selectivity from CMF to DMF: 80%; Yield from CMF to DMF: 76%.

Example 2

Synthesis of 5-methylfuran-2-carbaldehyde (MF) from 5-(chloromethyl)furfural (CMF)

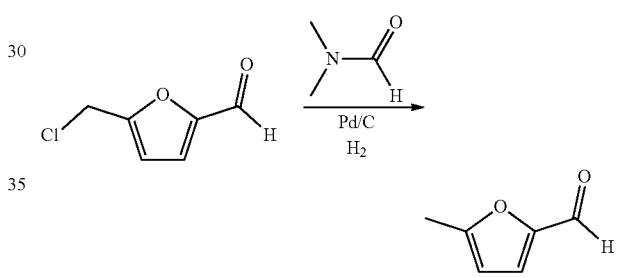

In a 250 mL Parr container (cooled to room temperature) was added 5.0012 g (34.596 mmol) of CMF (97%) followed by 25 mL of DMFD and under Argon 50 mg of 10% Pd/C. The reaction mixture was charged with $H_2$ up to 2 psi (charged and purged 4 times to 20 psi). When a 1 psi drop was observed, the flask was refilled to 2 psi until 65 psi was reached. After about 73 minutes, the reaction mixture was diluted in 100 ml volumetric flask with dichloromethane and an aliquot was taken for analysis by GCMS coupled with FID. Selectivity from MF to CMF: 99%; conversion from MF to CMF: 97%.

Example 3

Synthesis of 2,5-dimethylfuran (DMF) from 5-methylfuran-2-carbaldehyde (MF)

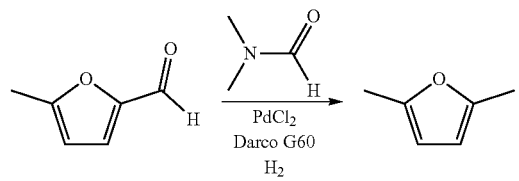

To a 250 ml Parr Shaker, 3.8051 g (34.51 mmol) of MF was added followed by 25 ml of DMFD and under Argon 100 mg of PdCl$_2$ and 500 mg of carbon Darco G60. The reaction was then charged with H$_2$ up to 50 psi (charged and purged 4 times). When a 10 psi drop was observed, the flask was recharged to 50 psi. After about 105 minutes, the reaction mixture was diluted to 100 ml and an aliquot was taken for analysis by GCMS coupled with FID. Selectivity from MF to DMF: 68%; conversion from MF to DMF: 100%; conversion from MF to (5-methylfuran-2-yl)methanol (MFA): 96%.

Example 4

Synthesis of 2,5-dimethylfuran (DMF) from 5-(chloromethyl)furfural (CMF)

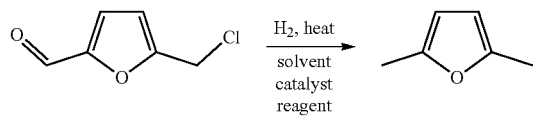

This Example demonstrates the production of 2,5-dimethylfuran (DMF) from 5-(chloromethyl)furfural (CMF) using various catalysts, solvents and other reagents.

To a 250 ml Parr shaker bottle was added CMF (5 g, 34.62 mmol) and 25 ml of Solvent A (as listed in Table 1 below). The CMF was dissolved in a mixture of organic Solvent A and Reagent B (as listed in Table 1 below), by stirring at room temperature for 5-10 minutes. Then, the catalyst (50 mg of Pd on support, as listed in Table 1 below) was either immersed in Reagent B up to the incipient wetness point and transferred to the container, or added directly into the container under argon. The reaction mixture was heated to 30-35° C., and the reaction flask was installed into the Parr Shaker. The flask was charged with hydrogen up to 50 psig (charged and purged 4 times to 20 psig). The flask was shaken to initiate the reaction, and the flask was refilled to 50 psig every time the pressure was observed to drop to about 40 psig. After 180 psig of hydrogen was consumed (2.96 eq of hydrogen), the Parr Shaker was stopped, and hydrogen was flushed out of the flask. The reaction mixture was then transferred into a 100 ml volumetric flask and diluted with acetone. An aliquot of the reaction mixture was taken, and products were quantitatively measured on GC.

TABLE 1

Summary of reactions and results

| Catalyst | CMF loading$^a$ | Solvent A, weight % | Reagent B, weight % | Reaction time | DMF selectivity (%) | DMF yield (%) |
|---|---|---|---|---|---|---|
| Pd/Al$_2$O$_3$ | 16% | Toluene, 77% | DMPU 23% | 120 min | 82-84 | 82-84 |
| Pd/Al$_2$O$_3$ | 16% | — | DMPU 100% | 120 min | 17 | 15 |
| Pd/Al$_2$O$_3$ | 16% | Toluene, 77% | DMI 23% | 70 min | 63 | 63 |
| Pd/Al$_2$O$_3$ | 16 | Toluene, 78% | TMU 22% | 186 min | 59 | 59 |

TABLE 1-continued

Summary of reactions and results

| Catalyst | CMF loading[a] | Solvent A, weight % | Reagent B, weight % | Reaction time | DMF selectivity (%) | DMF yield (%) |
|---|---|---|---|---|---|---|
| Pd/Al$_2$O$_3$ | 16 | — | TMU 100% | 300 min | 61 | 61 |
| Pd/Al$_2$O$_3$ | 16 | — | DMA 100% | 86 min | 36 | 17 |
| Pd/Al$_2$O$_3$ | 16 | — | DMFD 100% | 120 min | 83 | 83 |
| Pd/Al$_2$O$_3$ | 26 | — | DMFD 100% | 120 min | 81 | 81 |
| Pd/C | 16 | — | DMFD 100% | 70 min | 82 | 82 |
| Pd/C | 16 | Toluene, 48% | DMFD 52% | 48 min | 82 | 82 |
| Pd/Al$_2$O$_3$ | 16 | Dowtherm™ G, 78% | DMFD 18% | 222 min | 64 | 59 |

[a]CMF % loading = mass of CMF per total volume of reaction in solvent mix (Solvent A + Reagent B)

Example 5

Synthesis of Methylfuran (MF) from Furfural

This Example demonstrates the synthesis of methylfuran from furfural. To a 250 mL parr hydrogenation flask was added palladium (II) chloride (199.0 mg), Darco G-60 activated carbon (999.0 mg), dimethylpropyleneurea (5 ml), and toluene (15 ml). The flask was then sealed and placed into a Parr hydrogenation apparatus. The headspace was then purged 4× with 10 psig of hydrogen. The flask was then pressurized with hydrogen to 20 psig and the bottle was shaken for 20 minutes. After the metal reduction step, the flask was then depressurized from hydrogen and furfural (3.314 g, 34.492 mmol) was then added to the flask via pipette transfer using an additional 5 ml of toluene. The flask was then re-purged with hydrogen in a similar manner as described above, and the flask was filled with hydrogen to 50 psig, and the reduction was started. The reaction temperature and consumption of hydrogen over time were monitored, and the values are summarized in Table 2 below.

TABLE 2

| Time (min) continuous | Temperature Reaction (° C.) | Total Hydrogen Consumed (mmol) |
|---|---|---|
| 3.7 | 27 to 29 | 6.63 |
| 7.5 | 30 | 12.16 |
| 11.3 | 31 | 17.69 |
| 15.2 | 33 | 23.22 |
| 19.3 | 33 | 29.85 |
| 23.5 | 34 | 35.38 |
| 28.3 | 34 | 40.91 |
| 33.9 | 33 | 46.43 |
| 41.5 | 32 | 51.95 |
| 52.8 | 30 | 57.47 |
| 72.4 | 29 | 62.98 |
| 105.6 | 28 | 68.49 |

After about 106 minutes, the flask was depressurized and removed from the apparatus. The reaction mixture was then diluted to 100 ml in acetone, followed by a 5× dilution in acetone for GCMS analysis.

For the GCMS analysis, 1 μL of sample/standard was injected into an Agilent 6890 GC with FID detection with a 5:1 split ratio at a flow rate of 2.3 mL/min of helium carrier gas and onto the Agilent 5975 MSD with a split ratio of 25:1 at a flow rate of 1.5 mL/min of helium carrier gas. The temperature program started with an initial temperature of 35° C. and ramped up to a final temperature of 240° C. at 60 C/min and was held at 240° C. for 4 minutes. 2-Methylfuran was observed at 1.83 minutes for MS detection and at 1.86 minutes for FID detection. Thus, based on this GCMS analysis, 2-methylfuran was observed to be produced.

Example 6

Synthesis of 2,5-dimethylfuran (DMF) from 5-(chloromethyl)furfural (CMF)

This Example demonstrates the synthesis of DMF from CMF. To a 250 ml Parr hydrogenation bottle was added CMF (5 g; 34 mmol). Dowtherm-G (10 ml) was then added and the CMF was allowed to dissolve with light mixing under ambient conditions for a few minutes until a homogeneous solution was observed. In a separate vial, dimethylformamide (2 ml) was then added to 5% Pd/Alumina (994.3 mg) and the resulting slurry was mixed under ambient conditions for about 30 seconds. The slurry was then pipetted into the reaction flask, and 3 mL of dimethylformamide was used to quantitatively transfer the catalyst. Then, 10 mL of Dowtherm-G was used to wash the residual dimethylformamide from the vial into the reaction flask. The mixture was then heated to about 25° C. before placing the reaction flask into a Parr Shaker. The head space of the flask and the ballast connected to the hydrogen cylinder were then flushed with hydrogen (15 psig of hydrogen in the bottle head space) for about 1 minute. The flask was then purged 4× with 10 psig of hydrogen and filled to 40 psig. The first ballast reading was then taken and the pressure was increased to 50 psig. The consumption of hydrogen over time was monitored, and the values are summarized in Table 3 below.

TABLE 3

| Time (min) continuous | Total Hydrogen Consumed (mmol) |
|---|---|
| 4.6 | 6.702 |
| 9.8 | 13.415 |
| 15.9 | 19.004 |
| 22.0 | 24.602 |
| 28.6 | 30.178 |
| 36.5 | 35.771 |
| 45.8 | 42.464 |
| 56.4 | 48.047 |
| 68.6 | 53.636 |
| 83.0 | 59.231 |
| 100.0 | 64.826 |
| 123.0 | 70.421 |
| 150.0 | 77.132 |
| 175.1 | 83.850 |
| 222 | 88.321 |

The yield of DMF was observed to be about 59%, and the selectivity of DMF was observed to be about 64%. 5-Methylfurfural was also observed to have been produced.

What is claimed is:

1. A method of producing a compound of formula (I'):

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
the method comprising converting a compound of formula (A) to the compound of formula (I') in the presence of hydrogen, a catalyst and a reagent of formula (i), (ii) or (iii), or any combination thereof,
wherein:
the compound of formula (A) is:

wherein:
R$^{1a}$ is C$_m$ alkyl, or —(CH$_2$)$_m$Y, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo; and
the reagent of formula (i) is:

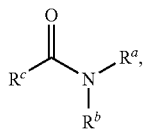
(i)

wherein:
each R$^a$, R$^b$ and R$^c$ is independently H, aliphatic, aryl, or heteroaryl; or
R$^a$ and R$^b$ are taken together with the nitrogen atoms to which they are connected to form a cyclic moiety having at least 3 ring atoms; provided that when R$^c$ is H or methyl, then one of R$^a$ and R$^b$ is other than methyl; and
the reagent of formula (ii) is:

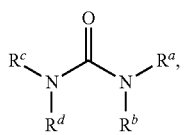
(ii)

wherein:
(A) each R$^a$, R$^b$, R$^c$ and R$^d$ is independently H, aliphatic, aryl or heteroaryl; or
(B) R$^a$ and R$^b$ are taken together with the nitrogen atoms to which they are connected to form a cyclic moiety having at least 3 ring atoms; and each R$^c$ and R$^d$ is independently H, aliphatic, aryl or heteroaryl; or
(C) each R$^a$ and R$^b$ is independently H, aliphatic, aryl or heteroaryl; and R$^c$ and R$^d$ are taken together with the nitrogen atoms to which they are connected to form a cyclic moiety having at least 3 ring atoms; or
(D) R$^a$ and R$^b$ are taken together with the nitrogen atoms to which they are connected to form a cyclic moiety having at least 3 ring atoms; and R$^c$ and R$^d$ are taken together with the nitrogen atoms to which they are connected to form a cyclic moiety having at least 3 ring atoms; or
(E) each R$^a$ and R$^c$ is independently H, aliphatic, aryl or heteroaryl; and R$^b$ and R$^d$ are taken together with the nitrogen atoms to which they are connected to form a cyclic moiety having at least 5 ring atoms; or
(F) each R$^b$ and R$^d$ is independently H, aliphatic, aryl or heteroaryl; and R$^a$ and R$^c$ are taken together with the nitrogen atoms to which they are connected to form a cyclic moiety having at least 5 ring atoms; and the reagent of formula (iii) is:

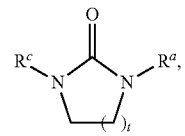
(iii)

wherein:
each R$^a$ and R$^c$ is independently H, aliphatic, aryl or heteroaryl; and
t is an integer greater than or equal to 0.

2. The method of claim 1, wherein the compound of formula (I') is a compound of formula (I-a) or (I-b):

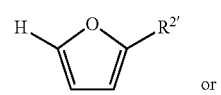
(I-a)

or

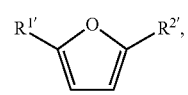
(I-b)

wherein R$^{1'}$ is C$_m$ alkyl, wherein m is an integer greater than or equal to 1.

3. The method of claim 1, wherein the compound of formula (I') is

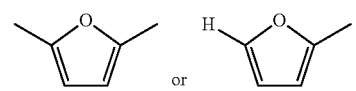

4. The method of claim 1, wherein the compound of formula (A) is a compound of formula (A-i) or (A-ii):

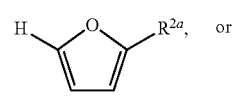
(A-i)

or

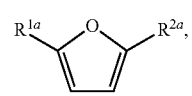
(A-ii)

wherein m is an integer greater than or equal to 1.

5. The method of claim 1, wherein R$^{1a}$ is C$_m$ alkyl.
6. The method of claim 1, wherein R$^{1a}$ is —(CH$_2$)$_m$Y.
7. The method of claim 1, wherein R$^{2a}$ is —(CH$_2$)$_{n-1}$CH(O).
8. The method of claim 1, wherein R$^{2a}$ is —(CH$_2$)$_n$OH.
9. The method of claim 1, wherein R$^{2a}$ is —(CH$_2$)$_n$X.
10. The method of claim 1, wherein the compound of formula (A) is

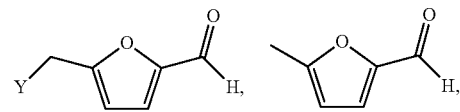

-continued

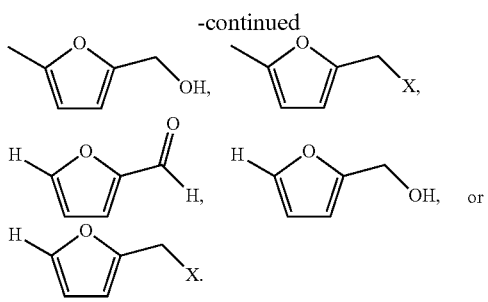

11. The method of claim 1, wherein the compound of formula (A) is:

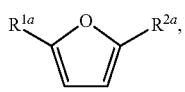
(A)

wherein:
R$^{1a}$ is —(CH$_2$)$_m$Y, wherein:
m is an integer greater than or equal to 1; and
Y is halo; and
R$^{2a}$ is —(CH$_2$)$_{n-1}$CH(O), wherein:
n is an integer greater than or equal to 1.

12. The method of claim 1, wherein the compound of formula (A) is:

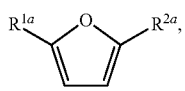
(A)

wherein:
R$^{1a}$ is C$_m$ alkyl, wherein:
m is an integer greater than or equal to 1; and
R$^{2a}$ is —(CH$_2$)$_{n-1}$CH(O), wherein:
n is an integer greater than or equal to 1.

13. The method of claim 1, wherein the compound of formula (A) is:

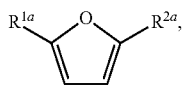
(A)

wherein:
R$^{1a}$ is C$_m$ alkyl, wherein:
m is an integer greater than or equal to 1; and
R$^{2a}$ is —(CH$_2$)$_n$OH, wherein:
n is an integer greater than or equal to 1.

14. The method of claim 1, wherein the compound of formula (A) is:

(A)

wherein:
R$^{1a}$ is H; and
R$^{2a}$ is —(CH$_2$)$_{n-1}$CH(O), wherein:
n is an integer greater than or equal to 1.

15. The method of claim 1, wherein the compound of formula (A) is:

(A)

wherein:
R$^{1a}$ is H: and
R$^{2a}$ is —(CH$_2$)$_n$OH, wherein:
n is an integer greater than or equal to 1.

16. The method of claim 1, wherein the compound of formula (A) is:

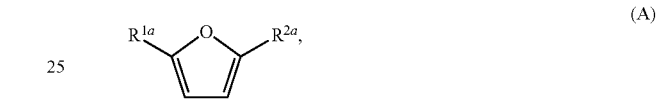
(A)

wherein:
R$^{1a}$ is H: and
R$^{2a}$ is —(CH$_2$)$_n$X, wherein:
n is an integer greater than or equal to 1; and
X is halo.

17. The method of claim 1, wherein the compound of formula (A) is:

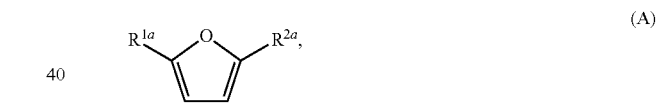
(A)

wherein:
R$^{1a}$ is C$_m$ alkyl, wherein:
m is an integer greater than or equal to 1; and
R$^{2a}$ is —(CH$_2$)$_n$X, wherein:
n is an integer greater than or equal to 1; and
X is halo.

18. The method of claim 1, wherein Y is chloro.
19. The method of claim 1, wherein X is chloro.
20. The method of claim 1, wherein the reagent of formula (i), (ii) or (iii) is selected from the group consisting of

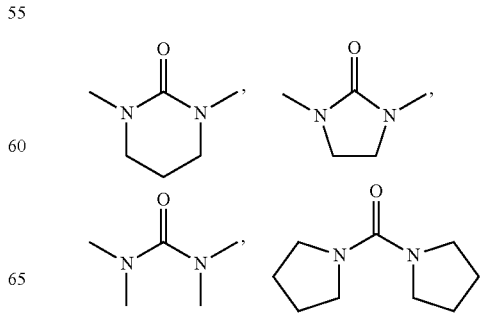

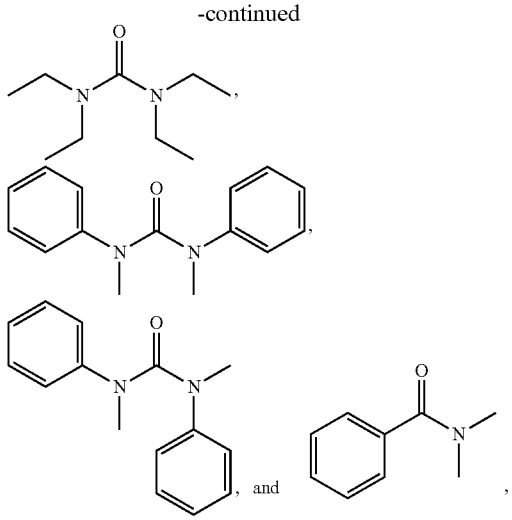

or any combinations thereof.

21. The method of claim 1, wherein the compound of formula (A) is converted to the compound of formula (I') in the further presence of acid.

22. The method of claim 1, wherein the compound of formula (A) is converted to the compound of formula (I') in the further presence of solvent.

23. The method of claim 22, wherein the solvent comprises organic solvent.

24. The method of claim 22, wherein the solvent comprises aromatic solvent.

25. The method of claim 22, wherein the solvent comprises at least one mono-aryl compound, at least one di-aryl compound, or at least one tri-aryl compound, or any mixtures thereof.

26. The method of claim 25, wherein the at least one mono-aryl compound is toluene or para-xylene.

27. A method of producing 2,5-dimethylfuran, comprising:
   a) providing (5-methylfuran-2-yl)methanol;
   b) converting the (5-methylfuran-2-yl)methanol to 2-(chloromethyl)-5-methylfuran in the presence of an acid; and
   c) reducing the 2-(chloromethyl)-5-methylfuran to produce 2,5-dimethylfuran.

28. The method of claim 27, wherein the (5-methylfuran-2-yl)methanol is provided by:
   i) providing 5-methylfuran-2-carbaldehyde; and
   ii) converting the 5-methylfuran-2-carbaldehyde to (5-methylfuran-2-yl)methanol in the presence of acid, hydrogen and a catalyst.

29. The method of claim 27, wherein the (5-methylfuran-2-yl)methanol is provided by:
   i) providing 5-(chloromethyl)furfural;
   ii) converting the 5-(chloromethyl)furfural to 5-methylfuran-2-carbaldehyde in the presence of hydrogen and a catalyst; and
   iii) converting the 5-methylfuran-2-carbaldehyde in the presence of acid, hydrogen and a catalyst.

* * * * *

UNITED STATES PATENT AND TRADEMARK OFFICE
CERTIFICATE OF CORRECTION

PATENT NO. : 9,908,862 B2
APPLICATION NO. : 14/912052
DATED : March 6, 2018
INVENTOR(S) : Dimitri A. Hirsch-Weil et al.

It is certified that error appears in the above-identified patent and that said Letters Patent is hereby corrected as shown below:

In the Specification

Column 4, Line 36:
"In other aspects, provided herein are also compositions that include any of the compounds of formula (A), catalysts, hydrogen, and amine or urea reagents described herein. In some embodiments, the compositions may also include any of the acids and/or solvents described herein."

Should be changed to:
-- In other aspects, provided herein are also compositions that include any of the compounds of formula (A), catalysts, hydrogen, and amide or urea reagents described herein. In some embodiments, the compositions may also include any of the acids and/or solvents described herein. --

Column 8, Line 17:
"The alkylfurans (e.g., the compounds of formula (I')), the furan compounds (e.g., the compounds of formula (A)), the catalysts, the acids, the hydrogen, the amine or urea reagents and the solvents, as well as the reaction conditions to produce the compounds of formula (I') are each described in further detail below."

Should be changed to:
-- The alkylfurans (e.g., the compounds of formula (I')), the furan compounds (e.g., the compounds of formula (A)), the catalysts, the acids, the hydrogen, the amide or urea reagents and the solvents, as well as the reaction conditions to produce the compounds of formula (I') are each described in further detail below. --

Column 15 bridging to 16, Line 65:
"The amounts of acid present in the reaction mixture may vary based on the compound of formula (A), the catalyst, the amount of hydrogen, and the amine or urea reagent. In certain variations, the amount of acid present in the reaction mixture does not exceed an amount that would decrease the activity of the catalyst."

Signed and Sealed this
Eighteenth Day of April, 2023

Katherine Kelly Vidal
*Director of the United States Patent and Trademark Office*

Should be changed to:

-- The amounts of acid present in the reaction mixture may vary based on the compound of formula (A), the catalyst, the amount of hydrogen, and the amide or urea reagent. In certain variations, the amount of acid present in the reaction mixture does not exceed an amount that would decrease the activity of the catalyst. --